United States Patent [19]

Carlson

[11] Patent Number: 5,648,343
[45] Date of Patent: Jul. 15, 1997

[54] METHOD FOR TREATING LPS-MEDIATED DISORDERS

[75] Inventor: Russell W. Carlson, Athens, Ga.

[73] Assignee: The University of Georgia Research Foundation, Athens, Ga.

[21] Appl. No.: 202,968

[22] Filed: Feb. 28, 1994

[51] Int. Cl.$^6$ .......................... A61K 31/70; C07H 3/04; C07H 3/06; C07H 5/06
[52] U.S. Cl. .......................... 514/53; 536/17.2; 536/17.9; 536/18.7; 536/55; 536/123.13
[58] Field of Search .......................... 536/17.2, 17.9, 536/18.7, 55, 123.13; 514/53

[56] References Cited

U.S. PATENT DOCUMENTS

| | | | |
|---|---|---|---|
| 4,987,237 | 1/1991 | Myers et al. | 549/222 |
| 5,158,941 | 10/1992 | Jadhav et al. | 514/62 |

FOREIGN PATENT DOCUMENTS 0 536 969 A2   5/1992   European Pat. Off. .

OTHER PUBLICATIONS

Takahashi, et al., "Structural Requirements of Endotoxic Lipopolysaccharides and Bacterial Cell Walls in Induction of Interleuken-1," *Blood Purification*, 6:188–206 (1988).

Carlson et al., "The *Rhizobiaceae* lipopolysaccharides (LPSs)," Abstract, 5th International Symposium on the Molecular Genetics of Plant–Microbe Interactions, Sep. 9–14, 1990.

Hollingsworth & Carlson, "27–Hydroxyoctacosanoic Acid Is a Major Structural Fatty Acyl Component of the Lipopolysaccharide of *Rhizobium trifolii* ANU 843," *The Journal of Biological Chemistry*, 264:9300–9303 (1989).

Bhat & Carlson, "Structure of a Galacturonic Acid Containing Lipid A from *Rhizobium phaseoli* CE3," Abstract, The First Congress of the International Endotoxin Society, May 10–12, 1990.

Carlson, et al., "*Rhizobium* lipopolysaccharides: Their structures and evidence for their importance in the nitrogen–fixing symbiotic infection of their host legumes," Biochemical and Genetic Analysis of Gene Expression in Plants and Bacteria, Chapman and Hall, New York, London (1991).

Bhat, et al., "Distribution and Phylogenetic Significance of 27–Hydroxy–Octacosanoic Acid in Lipopolysaccharides form Bacteria Belonging to the Alpha–2 Subgroup of *Proteobacteria*," *International Journal of systematic Bacteriology*, 41:213–217 (Apr. 1991).

Bhat, et al., "Occurrence of Lipid A Variants with 27–Hydroxyoctacosanoic Acid in Lipopolysaccharides form Members of the Family *Rhizobiaceae*," *Journal of Bacteriology*, 173:2155–2159 (Apr. 1991).

Bhat & Carlson, "A New Method for the Analysis of Amide *Rhizobiaceae*," *Journal of Cellular Biochemistry*, Supplement 16D (1992), Keystone Symposia on Molecular & Cellular Biology, Mar. 5–27, 1992.

Carlson, et al., "*Rhizobium* lipopolysaccharides; their structures and evidence for their importance in the nitrogen–fixing symbiotic infection of their host legumes," *Plant Biotechnology and Development*, Chapter 5, pp. 33–44, CRC Press (1992).

Bhat & Carlson, "A new method for the analysis of amide–linked hydroxy fatty acids in lipid–As from gram–negative bacteria," *Glycobiology*, 2:535–539 (1992).

*Primary Examiner*—Gary L. Kunz
*Attorney, Agent, or Firm*—Needle & Rosenberg, P.C.

[57] ABSTRACT

A purified lipid A from *Rhizobium leguminosarum* biovar phaseoli CE3, as well as analogs and derivatives of the purified lipid A are provided. Compositions containing heterogenous mixtures of lipid A from *R. leguminosarum* bv. phaseoli CE3 are also provided. The lipid A provided herein can be combined with a pharmaceutically acceptable carrier. Methods of stimulating the immune system in a subject, treating or preventing toxic shock in a subject, and methods of treating and preventing a lipopolysaccharide mediated disorder in a subject using the novel lipid A are provided.

7 Claims, 25 Drawing Sheets

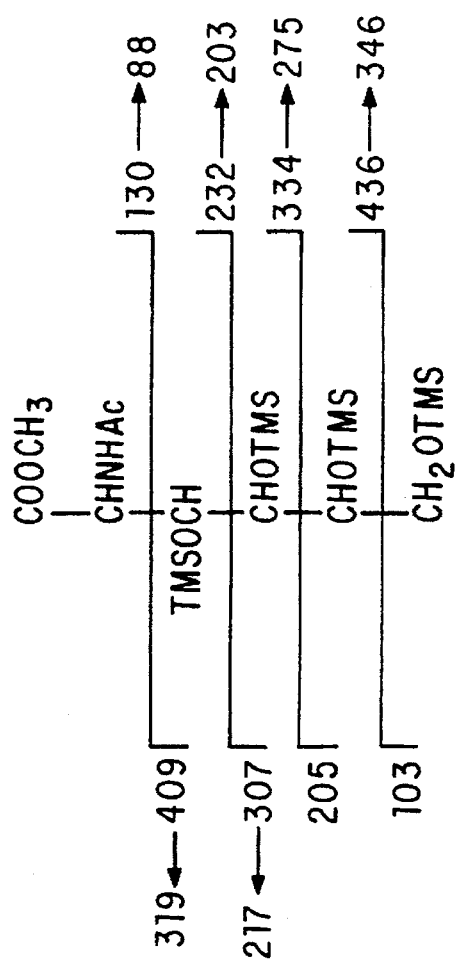
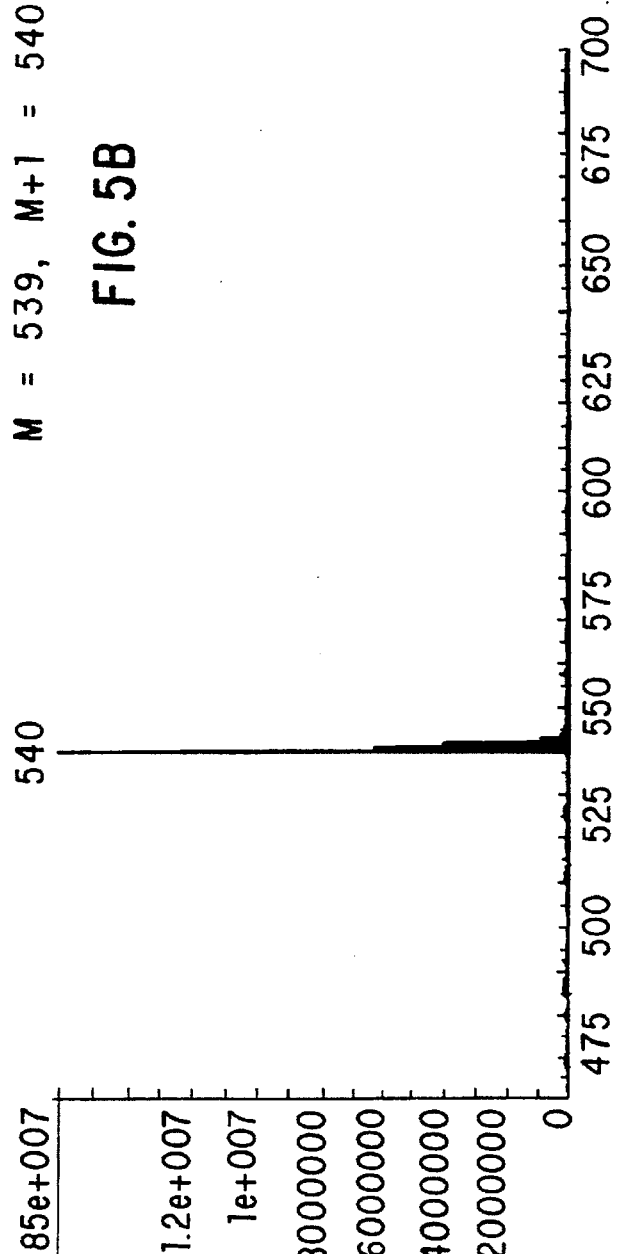
FIG. 5B
FIG. 5C $R_1$ = 3-Hydroxymyristyl, 3-hydroxypalmityl, or 3-hydroxystearyl substituents.

$R_2$ = 3-Hydroxymyristyl, 27-hydroxyoctacosanoyl, 3-hydroxypentadeconoyl, or 27-(3-hydroxybutoxy)-octacosanoyl substituents.

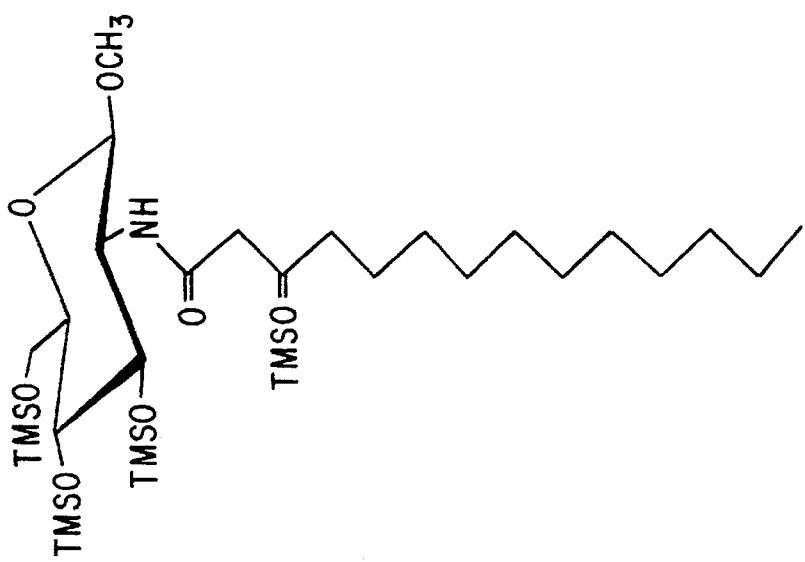
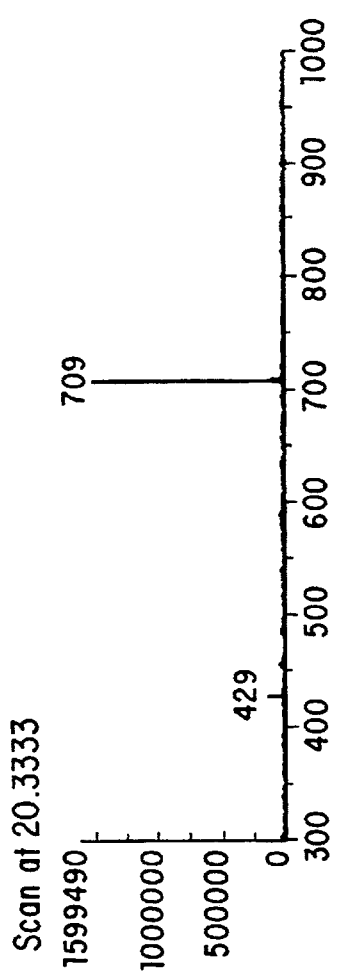
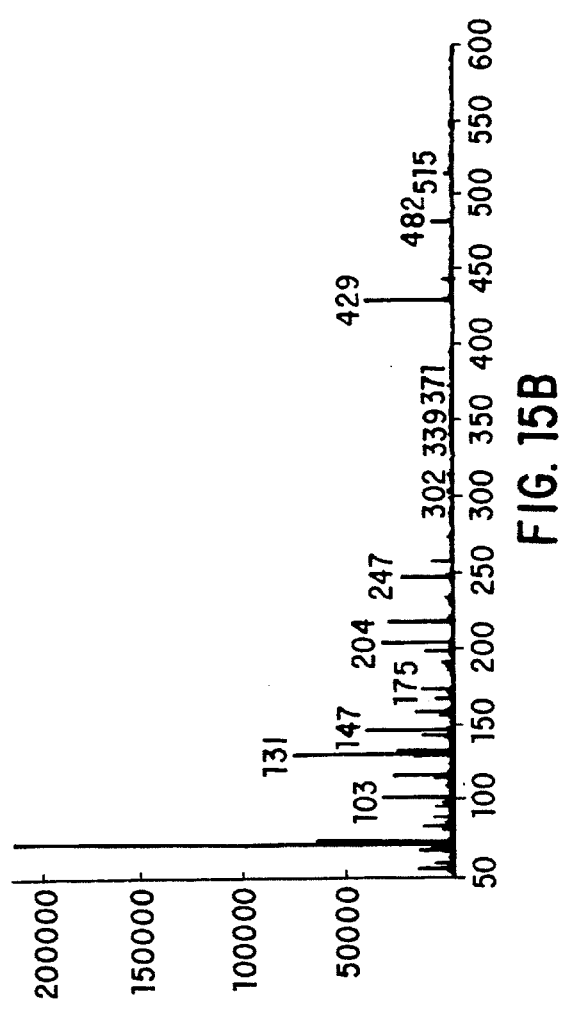
FIG. 15C
FIG. 15A
FIG. 15B

FIG. 15F  M+1 = 736

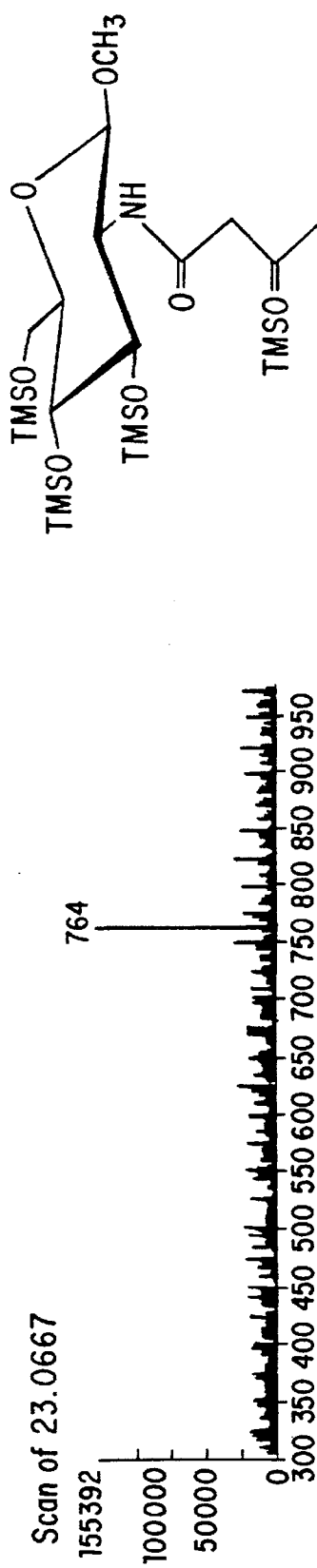
FIG. 15I
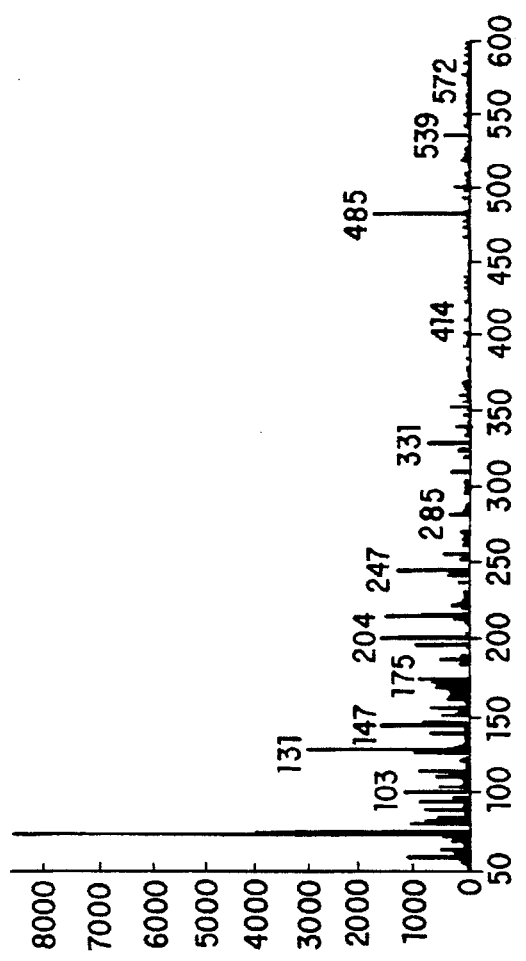
FIG. 15G
FIG. 15H

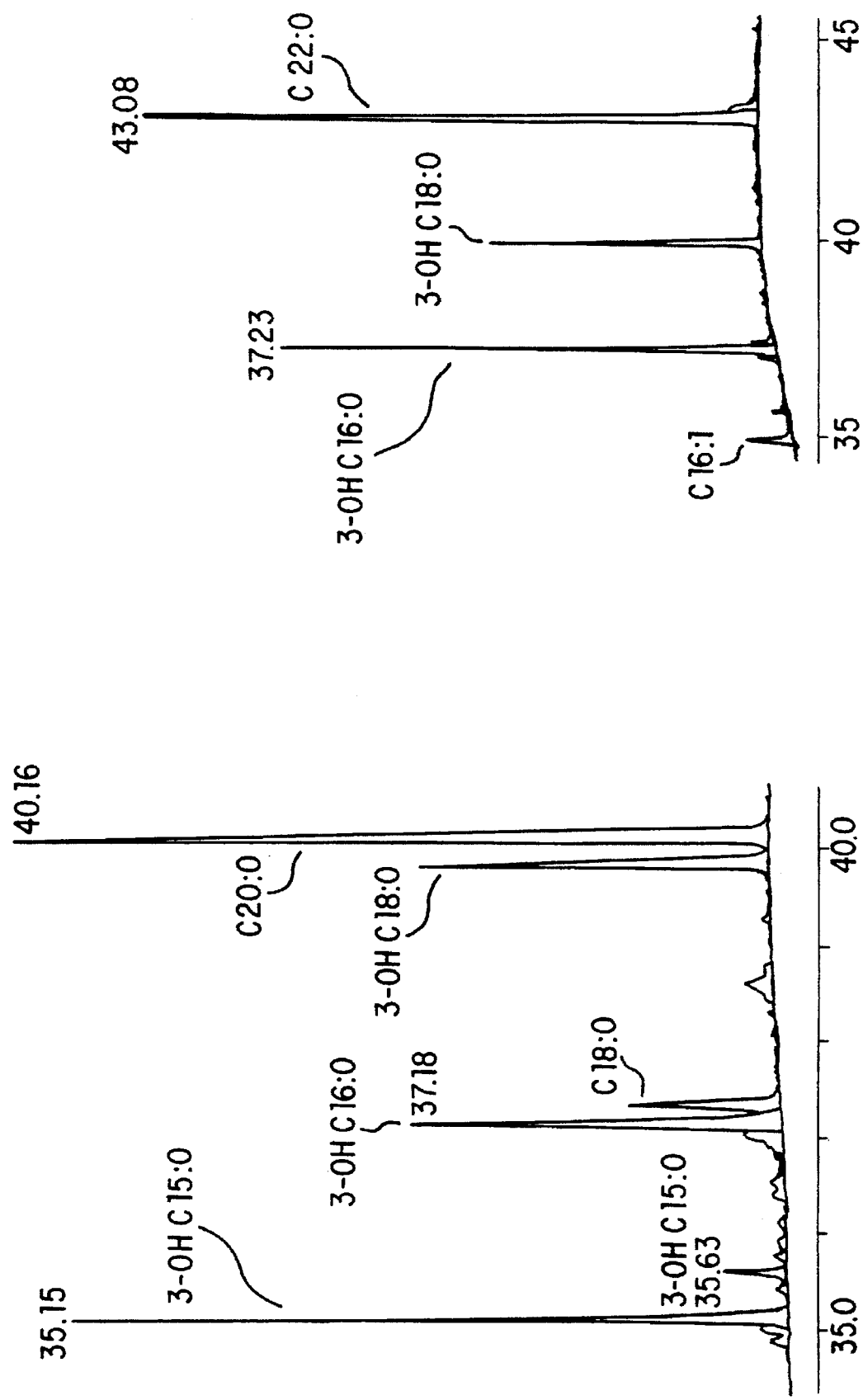

METHOD FOR TREATING LPS-MEDIATED DISORDERS

BACKGROUND OF THE INVENTION

This invention was supported in part by grant number R01 GM39583 from the National Institutes of Health. The United States government has certain rights in the invention.

1. Field of the Invention

This invention involves a novel Lipid A and methods using that Lipid A. In particular, this application discloses for the first time the structure of the Lipid A of *Rhizobium leguminosarum* biovar phaseoli CE3 and methods of using this unique Lipid A to stimulate the immune system, treat or prevent toxic shock in a septic subject and treat or prevent a lipopolysaccharide-mediated disorder in a subject.

2. Description Of Related Art

Bacteria of the Rhizobiaceae family are gram negative and able to form nitrogen-fixing relationships with legumes. The surface polysaccharides, including the lipopolysaccharides (LPSs), have been shown to play important roles in the symbiotic infection process.

Rhizobium and Bradyrhizobium LPS, as with others, have three structural regions: the lipid A, core oligosaccharide, and O-chain (or O side chain) polysaccharide. The rhizobial O-chain polysaccharides are highly variable and contain many methylated and deoxy glycosyl residues. See Stryer, *Biochemistry*, 2d Ed., W. H. Freeman and Co., New York, p. 74 (1981).

Before the discovery of the lipid A component of the LPS the term "endotoxin" was used to generically describe the effect of the LPS. The endotoxin from gram(—) bacteria is heat-stable, cell-associated, pyrogenic and potentially lethal. Lipid A is the causative agent of disorders such as septic or toxic shock and is related to other disorders such as Lyme disease.

The lipid A from enteric bacteria is somewhat variable. However, it is generally recognized that such a lipid A consists of a β-1,6-linked D-glucosamine disaccharide substituted at positions 4' and 1 by phosphomonoester groups. Fatty acids are linked to the hydroxyl and amino groups of the disaccharide to confer hydrophobicity to the lipid A. Also present in enterobacteria are amide and ester-linked D-3-hydroxy fatty acids, which consist of 14 carbons, e.g. β-hydroxymyristic acid. The C3-OH positions of these fatty acids may be further esterified with saturated fatty acids.

Despite these general characteristics, a degree of microheterogeneity occurs among diverse genera and species. Thus, *Neisseria* species produce 12 carbon 3-hydroxy fatty acids, saturated fatty acid substitution varies and the C'4-phosphoglucosamine disaccharide may contain a 4-amino-L-arabinose in salmonellae and *P. aeruginosa* as opposed to *E. coli* and Shigella. A very potent and toxic lipid A is a hexaacyl-1-4'-diphospholipid A. Structurally, a lipid A with one fewer or one more fatty acids will result in a biologically active, yet less toxic moiety. Removal of all fatty acids, however, deprives a particular lipid A of any biological activity. In addition, removal of either phosphate group results in significant loss of toxicity without loss of adjuvant activity. See Zinnser, *Microbiology*, 20th Ed., Appleton & Lange, Norwalk Conn., pp. 84–86 (1992).

As discussed above, the cell associated, heat stable toxin of gram-negative bacteria is the lipopolysaccharide (LPS). While both the O-antigen and the core regions modulate the toxic activity of the LPS, it is the lipid A region that possesses the biological activity of the endotoxin (26,31).

The structure of the lipid A from enteric bacteria (e.g. *E. coli*) is shown in FIG. 1. This structure is found in many gram-negative bacteria, and is the minimum structure required for toxic activity. Structural variations of this molecule that lack any one of the substituent groups; e.g. lacking a phosphate or fatty acyl substituent; are less toxic or not toxic (26,31). In addition, the minimal structure for viability of the bacterium requires the addition of two Kdo residues to C-6 of the terminal glucosamine residue (26).

In recent years, workers have discovered that endotoxin induced shock is caused by the ability of the LPS to stimulate host cells, such as macrophages, to produce excessive levels of cytokines (3,12,23). It is the excessive production of these cytokines, e.g. tumor necrosis factor (TNF) and interleukin I (IL-1), that results in toxic shock. At the present time it is probable that macrophages respond to lipid A by two possible mechanisms. The lust mechanism involves the interaction of lipid A with a receptor on the macrophage cell surface which results in the release of signals that stimulate the synthesis of cytokines. This mechanism occurs with relatively high concentrations (nM) of lipid A (20,25). The second mechanism involves the binding of the lipid A (or LPS) by a serum protein called the LPS binding protein (LBP). This LPS-LBP complex then interacts with a receptor (CD14) on the surface of the macrophage resulting, again, in the production of signals with stimulate the synthesis of cytokines (20,30,34,35,42). This second mechanism is active at low lipid A concentrations (pM) (20).

The potent biological activity of lipid A has directed numerous research efforts toward developing useful applications of this activity. First, the necessity of a minimal structure for bacterial viability has led workers to synthesize compounds which inhibit the synthesis of this structure, and thereby, act as a new class of antibiotics (15,16). These inhibitors are based on their ability to inhibit Kdo synthase activity. Second, the ability of lipid A to stimulate the immune system has resulted in the investigation of the use of lipid A, and modified lipid A structures and analogs, as therapeutic anti-tumor agents (33,36), and, more recently, as adjuvants for vaccine development (1). Third, therapeutic agents which inhibit the interaction of lipid A with macrophages have been investigated as treatments for sepsis (13). These agents, have been polyclonal or monoclonal antibodies against common structural regions of lipid A (the core oligosaccharide or lipid A) (6,7,11,13,18,28,38,41,44, 45), monoclonal antibodies against the LBP or CD14 proteins (2,11), and lipid A analogs which inhibit the binding of lipid A to LBP or CD14 (17,32). The use of antibodies in animal studies has warranted their testing in humans. Three different trials have given inconsistent results. However, in a subset of patients with gram-negative sepsis the results seemed to be beneficial and safe (13). The overall draw-back of this type of therapy is the high cost of acquiring these antibodies combined with the marginal benefits (as obtained in the recent clinical trials). Another useful approach is the use of lipid A analogs as antagonism for the toxic activity of lipid A. Several synthetic compounds have been examined (14,21,26,27,31,37), however the compound with the most potential is based on the lipid A from *Rhodobacter sphaeroides* (17,32) and on that from *Rhodobacter capsulatus* (FIG. 2) (19). This lipid A, which is unusual in that in contains unsaturated and 3-oxo fatty acyl residues, is not toxic and is a potent inhibitor of the ability of lipid A to stimulate cytokine production in an in vitro assay (17,22,32). Recently, a synthetic analog of this compound has been developed by Eisai (10) (FIG. 3) which is an even more potent lipid A antagonist.

The biological responses to LPS/Lipid A challenge are varied. Endotoxin is a potent pleiotropic biomodifier. Response to endotoxin challenge is species, dose, site, and mute dependent. Even small doses of lipid A cause extreme changes in body temperature, hematology, immunology, and endocrinology of the subject. Lethal doses lead to hypotension, disseminated intravascular coagulation, irreversible shock, and, ultimately, death.

Most animals exhibit neutropenia and rapid induction of fever and hypotension upon challenge with lipid A from gram(—) bacteria. Intracerebral dosage of endotoxin requires a significantly reduced quantity for similarly devastating results. The most sensitive animals to endotoxin are humans. For instance, only about 2 ng LPS/kg from *Salmonella abortus equi* induces granulocytosis, a 7-hour fever of about 2° C. maximal temperature rise, and increased plasma cortisol levels. As opposed to the biphasic fever curve in other animals, the human fever response is monophasic. A dose of about 100 µg LPS is lethal in humans.

Known hematologic responses to LPS injection include production of cytokines such as Interleukin-1 (IL-1), Interleukin-6 (IL-6) and tumor necrosis factor (TNF). Significant release of endotoxin into the circulatory system leads to disseminated intravascular coagulation. The Schwartzman reactions are classic examples of endotoxin induced clotting responses. See Zinnser, supra at p. 86.

Lipid A is cleared from the host when human peripheral blood monocytes and neutrophils begin to deacylate the lipid A with an acyloxyacyl hydrolase which removes fatty acids esterified to β-hydroxymyristate acid esters. This deacylation results in significant reduction in toxicity of the resulting modified lipid A. The deacylated lipid A does, however, retain some adjuvant activity and ability to modulate or antagonize further response to LPS.

Current treatment for lipid A challenge includes the use of polymyxin B. Polymyxin B is thought to form a complex with LPS and thereby prevent the toxin from acting. In addition, monoclonal antibodies to tumor necrosis factor may be helpful. Although such treatments are helpful in alleviating some of the devastating effects of lipid A toxicosis, they do not constitute a completely safe and effective treatment. Therefore, there still exists a need for novel, effective treatments for lipid A associated disorders. In addition, there exists a need for a lipid A which is a potent adjuvant without the related toxicity. Finally, there exists a need for a lipid A which can be used to treat or prevent LPS associated disorders. The present invention provides the discovery that the lipid A from *Rhizobium leguminosarum* biovar phaseoli CE3 satisfies these needs.

There are two reports which describe a lipid A structure from two different strains of *R. leguminosarum* bv trifolii (52,53). These reports provide incorrect structures for lipid A. Both of these reports describe structures which differ from each other, and which differ significantly from the structures described herein. Furthermore, the beneficial activities of the lipid A of this invention were not described, e.g., the use of this novel lipid A and its analogs as therapeutic agents to stimulate the immune system, as adjuvants for vaccines, and as lipid A antagonists to prevent or treat sepsis.

SUMMARY OF THE INVENTION

This invention provides novel lipid A structures derived from *Rhizobium leguminosarum*. In addition, this invention provides methods of using that novel lipid A to stimulate the immune system, prevent toxic shock in a subject and treat or prevent a lipopolysaccharide mediated disorder in a subject.

This invention provides a purified lipid A from *Rhizobium leguminosarum* biovar phaseoli CE3 and analogs and derivatives of that lipid A. See, generally, FIG. 13. The general structure (A) for the lipid A of the invention is as follows:

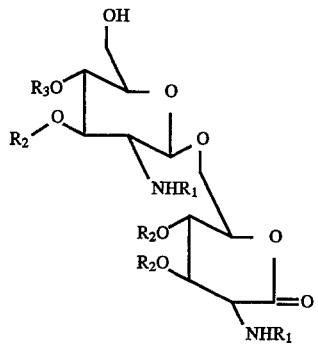

Referring to the above structure, $R_1$ is $H_3C—(CH_2)_m—COR_4H—CH_2—CO—$, $R_4$ is either H, $H_3C—(CH_2)_{10}—CO—$ or $H_3C—(CH_2)_{12}—CO—$, and m is 10, 12 or 14. In addition, $R_2$ is either $H_3C—CHOR_5—(CH_2)_{25}—CO—$ or $H_3C—(CH_2)_nCOR_6H—CH_2—CO—$ where $R_5$ is H or $H_3C—CHOH—CH_2—CO—$. Also, $R_6$ is either H, $H_3C—(CH_2)_{10}—CO—$ or $H_3C—(CH_2)_{12}—CO—$ and n is either 10, 12 or 14 and $R_3$ is H, $—PO_4$ or

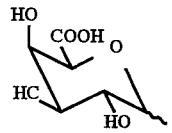

where the wavy line represents either an alpha or beta alkyl linkage. In a more preferable embodiment, still referring to the above general structure (A), R, is $H_3C—(CH_2)_{10}—CHOH—CH_2—CO—$. In addition, $R_2$ is either $H_3C—CHOR_4—(CH_2)_{25}—CO—$ or $H_3C—(CH_2)_{10}CHOH—CH_2—CO—$ where $R_4$ is $H_3C—CHOH—CH_2—CO—$. $R_3$ is

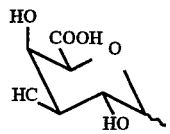

where the wavy line represents an alpha alkyl linkage and $R_5$ is $H_3C—(CH_2)_{12}-CHOH—CH_2—CO—$.

In addition, the present invention provides analogs of lipid A having the general structure (B) as follows:

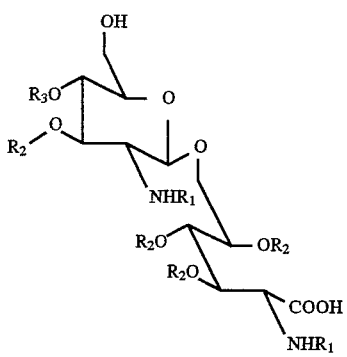

Referring to the above structure, $R_1$ is $H_3C$—$(CH_2)_m$—$COR_4H$—$CH_2$—$CO$—, $R_4$ is either H, $H_3C$—$(CH_2)_{10}$—$CO$— or $H_3C$—$(CH_2)_{12}$—$CO$—, and m is 10, 12 or 14. In addition, $R_2$ is either $H_3C$—$CHOR_5$—$(CH_2)_{25}$—$CO$— or $H_3C$—$(CH_2)_nCOR_6H$—$CH_2$—$CO$— where $R_5$ is H or $H_3C$—$CHOH$—$CH_2$—$CO$—. Also, $R_6$ is either H, $H_3C$—$(CH_2)_{10}$—$CO$— or $H_3C$—$(CH_2)_{12}$—$CO$— and n is either 10, 12 or 14 and $R_3$ is H, —$PO_4$ or

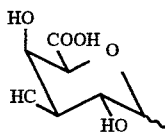

where the wavy line represents either an alpha or beta alkyl linkage. In a more preferable embodiment, also referring to the above general structure (B), $R_1$ is $H_3C$—$(CH_2)_{10}$—$CHOH$—$CH_2$—$CO$—. In addition, $R_2$ is either $H_3C$—$CHOR_4$—$(CH_2)_{25}$—$CO$— or $H_3C$—$(CH_2)_{10}CHOH$—$CH_2$—$CO$— where $R_4$ is $H_3C$—$CHOH$—$CH_2$—$CO$—. $R_3$ is

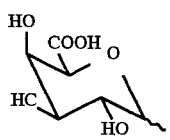

where the wavy line represents an alpha alkyl linkage and $R_5$ is $H_3C$—$(CH_2)_{12}$—$CHOH$—$CH_2$—$CO$—.

The invention also provides compositions containing heterogenous mixtures of variations in the core lipid A from *R. leguminosarum* bv. phaseoli CE3 as shown in the general structures (A) and (B) and their analogs shown above. Furthermore, this invention provides the above analogs (general structures (A) and (B)) of lipid A combined with a pharmaceutically acceptable carrier.

In addition to the above compositions, also provided is a method of stimulating the immune system in a subject, comprising administering to the subject an immune system stimulating amount of a purified lipid A (as described above in reference to general structures (A) and (B)) from *R. leguminosarum*. A method of treating or preventing toxic shock in a subject, comprising administering to the subject an effective amount of the lipid A (as disclosed and described above in general structures (A) and (B)) is also disclosed. Finally, a method of treating or preventing a lipopolysaccharide mediated disorder in a subject, comprising administering to the subject a lipopolysaccharide mediated disorder inhibiting amount of the lipid A from *R. leguminosarum* bv. phaseoli CE3 (as disclosed and described in general structures (A) and (B) and the accompanying text above) is provided.

DETAILED DESCRIPTION OF THE PREFERRED EMBODIMENTS

Figure 2:
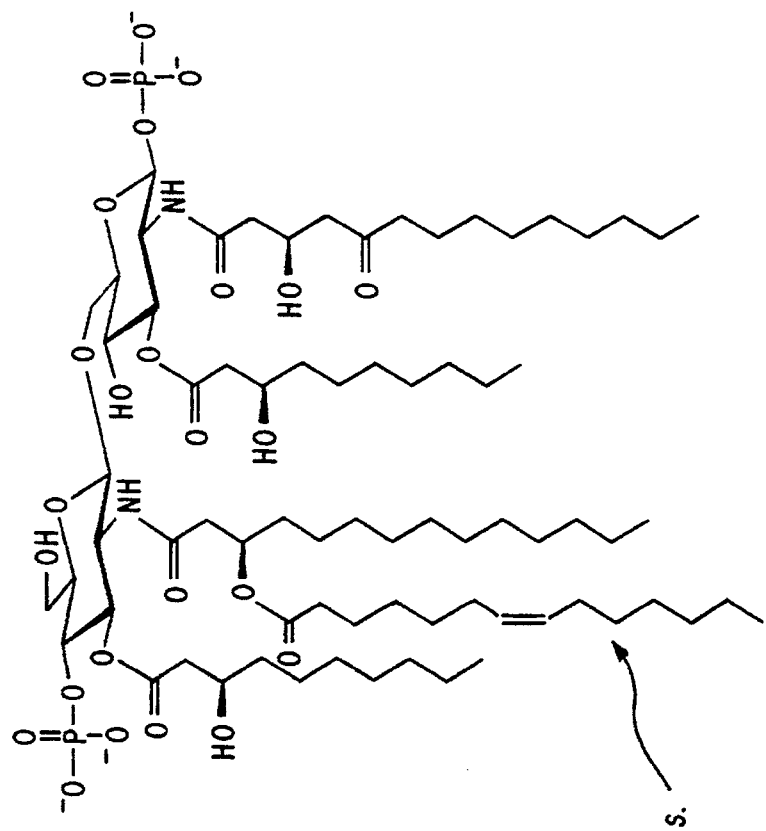
FIG. 2 shows the structure of the lipid A from *Rhodobacter sphaeroides* and *Rhodobacter capsulatus*.

As used in the claims and depending upon the context where used, "a" can mean one or more than one. Additionally, the "Rhizobium leguminosarum biovar phaseoli CE3" bacteria has recently been reclassified and a renamed "Rhizobium etli" strain (54). Therefore, the name "Rhizobium leguminosarum" is also meant to identify the strain of bacteria named "Rhizobium etli" and the terms are meant to be used interchangeably herein.

The novel lipid A structures provided by the present invention are disclosed below. In particular, the present invention provides a purified compound comprising the following formula (hereinafter referred to as general structure (A)):

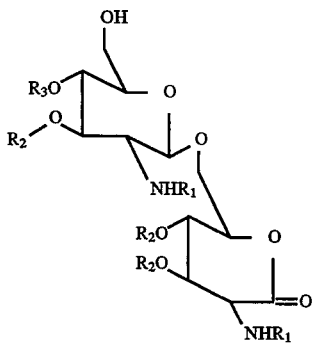

In this structure, $R_1$ is $H_3C-(CH_2)_m-COR_4H-CH_2-CO-$. In addition, in $R_1$, $R_4$ is one of the following moieties: H, $H_3C-(CH_2)_{10}-CO-$ or $H_3C-(CH_2)_{12}-CO-$. Also, in $R_1$, m is either 10, 12 or 14. $R_2$ is either $H_3C-CHOR_5-(CH_2)_{25}-CO-$ or $H_3C-(CH_2)_nCOR_6H-CH_2-CO-$. Furthermore, $R_5$ is either H or $H_3C-CHOH-CH_2-CO-$. $R_6$ is either H, $H_3C-(CH_2)_{10}-$ or $H_3C-(CH_2)_{12}-CO-$. In $R_2$, n is 10, 12 or 14. $R_3$ is selected from the group consisting of H, $-PO_4$ and where the wavy line represents either an

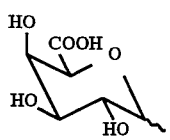

alpha or beta alkyl linkage.

In a preferred embodiment, the present invention provides a purified compound having the following formula:

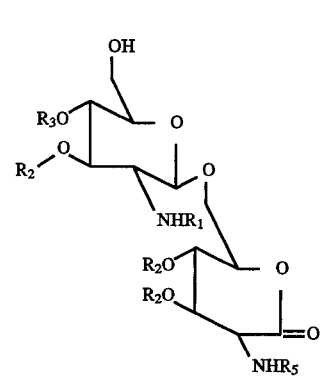

In this formula, $R_1$ is $H_3C-(CH_2)_{10}-CHOH-CH_2-CO-$. Furthermore, $R_2$ is either $H_3C-CHOR_4-(CH_2)_{25}-CO-$ or $H_3C-(CH_2)_{10}CHOH-CH_2-CO-$. $R_4$ is $H_3C-CH(OH)-CH_2-CO-$. $R_3$ is where the

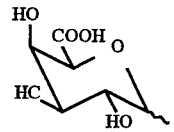

wavy line represents an alpha alkyl linkage. Finally, $R_5$ is $H_3C-(CH_2)_{12}-CHOH-CH_2-CO-$.

In another embodiment, the lipid A of this invention is a purified compound having the following formula (hereinafter referred to as general structure (B)):

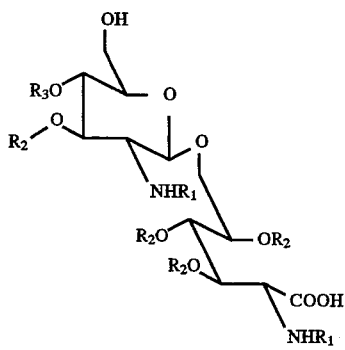

In this formula, $R_1$ is $H_3C-(CH_2)_m-COR_4H-CH_2-CO-$ where $R_4$ is either H, $H_3C-(CH_2)_{10}-CO-$ or $H_3C-(CH_2)_{12}-CO-$ and m is 10, 12 or 14. Next, $R_2$ is either $H_3C-CHOR_5-(CH_2)_{25}-CO-$ or $H_3C-(CH_2)_nCOR_6H-CH_2-CO-$ where $R_5$ is H or $H_3C-CHOH-CH_2-CO-$ and $R_6$ is H, $H_3C-(CH_2)_{10}-CO-$ or $H_3C-(CH_2)_{12}-CO-$ and n is 10, 12 or 14. Finally, $R_3$ is H, $-PO_4$ or wherein the

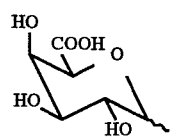

wavy line represents either an alpha or beta alkyl linkage.

In a preferred embodiment, this invention further provides purified lipid A compounds having the following formula:

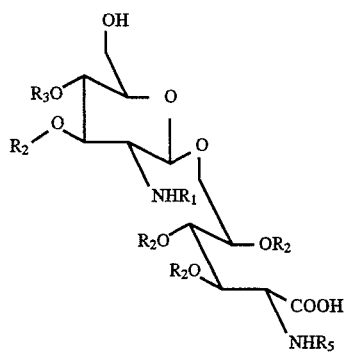

In this embodiment, $R_1$ is $H_3C-(CH_2)_{10}-CHOH-CH_2-CO-$. In addition, $R_2$ is either $H_3C-CHOR_4-(CH_2)_{25}-CO-$ or $H_3C-(CH_2)_{10}CHOH-CH_2-CO-$ where $R_4$ is $H_3C-CH(OH)-CH_2-CO-$. Also, $R_3$ is where

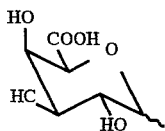

the wavy line represents an alpha alkyl linkage. Finally, $R_5$ is $H_3C-(CH_2)_{12}-CHOH-CH_2-CO-$.

The present invention also provides a compositions comprising a heterogenous mixture of the above-identified (general structures (A) and (B) and accompanying text) compounds. By "heterogenous mixture" it is intended that more than one purified lipid A analog of *R. leguminosarum* disclosed herein can occur in the same composition. No specific amount, ratio, or number of different lipid A analogs is necessary to form a heterogenous mixture. Such a mixture simply contains two or more different lipid A molecules as described by the structures discussed herein.

EXAMPLE I

Purification and analysis of *Rhizobium leguminosarum* biovar phaseoli CE3

Growth of Bacteria

*Rhizobium leguminosarum* biovar phaseoli CE3 was obtained from Dr. Dale Noel (Marquette University, Milwaukee, Wisc.). Bacteria were cultured in a tryptone/yeast extract medium supplemented with $Ca^{2+}$ as previously described (8,24). After growth to late log/early stationary phase the bacteria were harvested by centrifugation.

Lipopolysaccharide and Lipid A Purification

The LPS was extracted using hot phenol/water (39), treated with RNAse and purified by ultracentrifugation, or by gel filtration (9). Thus, with gel filtration, purity is indicated by the absence of proteins, nucleic acids, phospholipids and capsular polysaccharides and extracellular polysaccharides (9). With ultracentrifugation, the lipid A was released from the LPS by hydrolysis in aqueous 1% acetic acid (29) at 100° C. for 2 h. The released lipid A precipitated and was purified by centrifugation. The aqueous layer was extracted with methylene chloride and the lipid A in the organic layer was combined with the precipitate.

Thus, the lipid A purified by the above processes contains heterogenous mixtures of similar lipid A analogs (discussed further hereinbelow). In addition, the characterization/purification procedures result in further, novel lipid A analogs (the lactone analogs) which are likely not naturally present in *Rhizobium leguminosarum*.

Glycosyl Composition Analysis

Two methods were used to determine the glycosyl composition of the lipid A; the preparation and GLC-MS analysis of alditol acetates and of trimethylsilyl (TMS) methyl glycosides (43). In the case of alditol acetates, the carboxyl groups of the acidic glycosyl residues were reduced (converted to methyl esters) by methanolysis in methanolic 1M HCl at 80° C. for 2 h. The solvents were evaporated with a stream of nitrogen and the sample was reduced with a 10 mg/ml solution of $NaBD_4$ in water. The excess $NaBD_4$ was destroyed with several drops of glacial acetic acid, and borate was removed by repeated (4 to 5) evaporations from methanol/acetic acid (9:1). The samples were then hydrolyzed, reduced and acetylated (43). The TMS methyl glycosides were prepared by methanolysis in methanolic 1M HCl at 80° C. for 18 h, N-acetylated, and trimethylsilylated (43). Analysis was performed by GLC-MS using either a 15 m DB1 column (J&W Scientific, Illinois), or a 50 m methyl silicone column (Quadrex Corporation), and a 30 m SP2330 column (Supelco) for alditol acetates. Some GLC-MS analyses required chemical ionization (CI), which was performed on a Hewlett-Packard 5985 GLC-MS system with an ion source temperature of 150° C. using ammonia as the reactant gas.

Fatty Acid Analysis

Total fatty acids were released by complete methanolysis, as described above for the preparation of TMS methyl glycosides. The resulting fatty acid methyl esters were analyzed by GLC-MS, using the columns as described above. Ester and amide-linked fatty acids were distinguished by preferential release of the ester-linked fatty acids using absolute (anhydrons) sodium methoxide as described by Wollenweber and Rietschel (40). Kraska methylation was attempted in order to characterize any amide-linked acyloxyacyl fatty acids (40). The amide-linked fatty acids were determined by mild methanolysis (4) via the preparation of TMS N-acylglucosamine methyl glycosides. Total fatty acids were removed from the lipid A by hydrazinolysis (40).

De-O-Acylation of Lipid A

Portions of the lipid A preparations were de-O-acylated in sodium methoxide (0.25M) at 35° C. for 16 h. The lipid A (2–8 mg) was suspended in $CHCl_3$, and anhydrous sodium methoxide (0.5M in methanol) was added to yield a final lipid A concentration of 2 mg/mL. Following incubation, the mixture was centrifuged (3000 xg) and the supernatant was removed and analyzed for released fatty acids. The precipitate was again treated with sodium methoxide (0.5M, without $CHCl_3$). The supernatants from the two methoxide treatments were combined, and the remaining precipitate fraction was dissolved in water, acidified to pH 4.0 with dilute acetic acid, and washed two times with hexane:chloroform (1:1, v:v) to remove residual fatty adds. Portions of the precipitated de-O-acylated lipid A were convened to the acid (COOH) form by passage through a Dowex 50-($H^+$) column, eluted with water and then with water:methanol (1:1).

Glycosyl Linkage Analysis

Permethylated alditol acetates were prepared using a modification of the Hakomori procedure as described by York et al. (43), and analyzed by 6LC-MS using a 30 m SP2330 column from Supelco. β-Elimination was carried out on the permethylated lipid A (prior to acid hydrolysis) by stirring overnight in 2M dimethylsulfoxide anion (potassium salt in dimethylsulfoxide. The β-elimination product was ethylated (using ethyl iodide) or trideuteromethylated using ethyl iodide or trideuteromethyl iodide, respectively. Alditol acetates were prepared and analyzed as described above (43). When necessary, the carboxymethyl groups of the permethylated samples were reduced using lithium triethylborodeuteride ("Superdeuteride") (Aldrich Chemical Co., Milwaukee, Wisc.) (43).

Location of the fatty acyl residues was determined by diazomethane methylation of the lipid A under neutral conditions, using silica gel as the catalyst (46), followed by the preparation and GLC-MS analysis of the partially methylated alditol acetates.

NMR Spectoscopy

Samples were exchanged several times with $D_2O$, dissolved in $D_2O$ and analyzed at 295° K. using a Bruker AM500 spectrometer. Chemical shifts were measured relative to the HOD resonance, which, in turn, was measured relative to sodium 3-trimethylsilylpropionate-2,2,3,3-$d_4$ (TSP).

High Resolution Mass Spectrometry

Fast atom bombardment mass spectrometry (FAB-MS) was performed using a VG ZAB-SE instrument (VG Analytical, Manchester, UK) using an ion-Tech xenon gun operated at 8 kV and 1 Ma in the positive mode or negative ion mode. Samples, 2–10 μg, were analyzed using thioglycerol as the matrix. Liquid secondary ion mass spectrometry (LSIMS) was performed using a JEOL HX110/HX110 mass spectrometer operated in the positive ion mode at 10 kV accelerating potential with a cesium iodide source. Samples were run in a thioglycerol matrix. Acquired spectra are averaged profile data as recorded by a JEOL complement data system. These spectra were acquired from m/z 0–3000 at a rate that would scan from m/z 1 to 6000 in 1 minute. A filtering rate of 300 Hz and an approximate resolution of 1500 were used in acquiring these spectra. Electrospray mass spectrometry (ES-MS), was performed using a SCIEX API-III mass analyzer operated in the positive ion mode with an orifice potential of 50 V. Spectra are the accumulation of 10 to 15 scans collected from 200–1200 a.m.u. with an incremental step of 1.0 a.m.u. Samples were dissolved in 20% aqueous acetonitrile containing 1% acetic acid and pumped into the mass spectrometer at a rate of 3 mL/min.

Composition Analysis

The *R. leguminosarum* bv phaseoli CE3 lipid A was measured for the presence of phosphate with negative results. Unlike the lipid A from enteric bacteria, this Rhizobium lipid A does not contain phosphate. Analysis of the TMS methylglycosyides revealed the presence of galacturonic acid (GalA), glucosamine (GleN), and an (initially) unidentified component which eluted from the column 2 min. prior to glucosamine. The galacturonic acid and glucosamine were present in a 1.00:0.79 ratio as measured from the uncorrected total ion current (TIC) peak areas.

The presence of galacturonic acid was confirmed by mild methanolysis, reduction of the carboxymethyl ester using $NaBD_4$, preparation of alditol acetates and analysis by GLC-MS. The GLC-MS analysis showed the presence of the alditol acetate of galactose having two deuterium atoms at C-6 (fragment ions m/z 219, 291, and 363) thereby proving the presence of galacturonic acid in the lipid A sample.

Figure 5A:
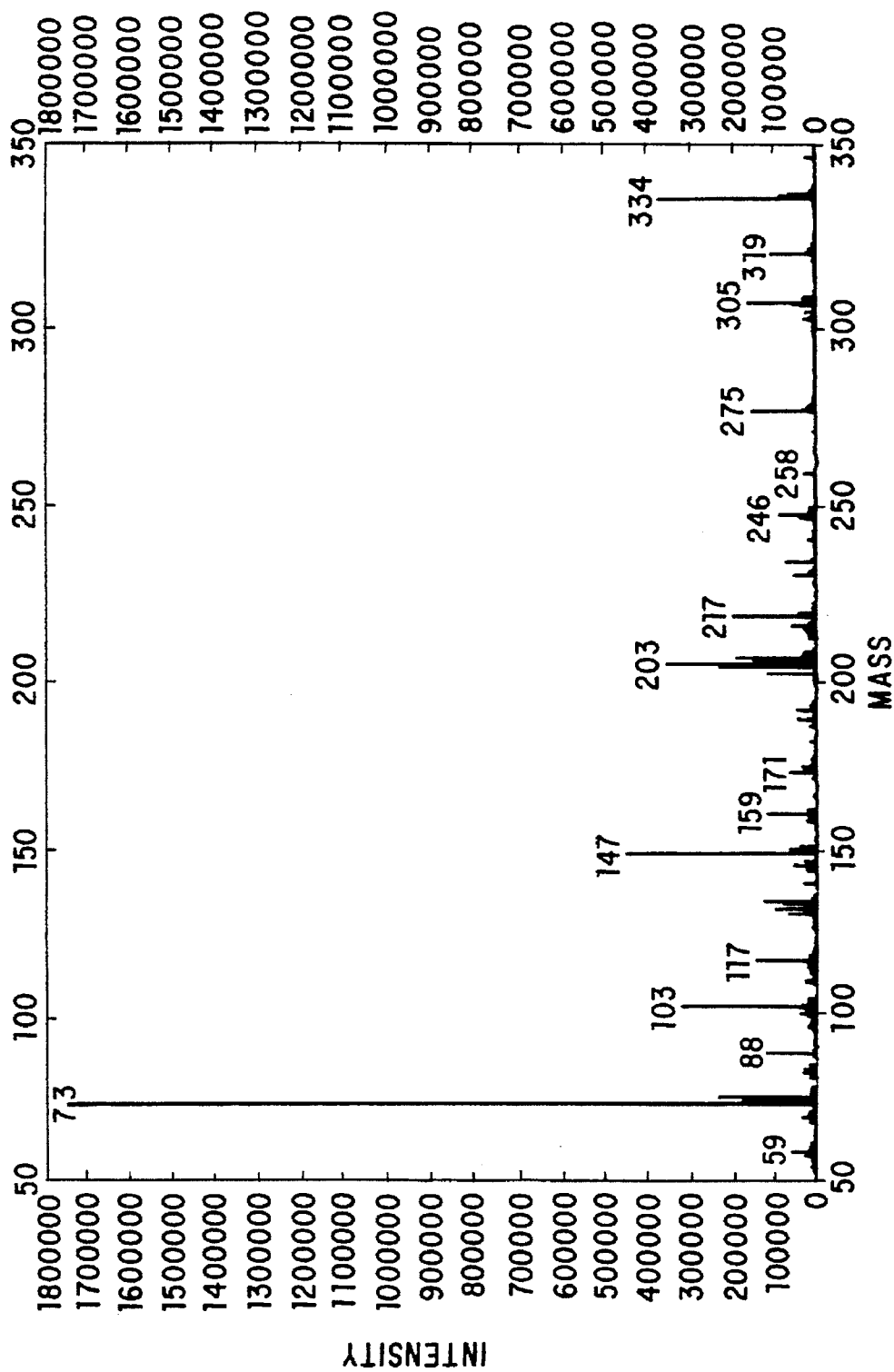
FIG. 5 shows the e.i.-m.s. (panel A) and c.i.-m.s. (panel B) spectra of the N-acetylated TMS derivative of methyl 2-aminogluconate from *R. leguminosarum* bv. phaseoli CE3 lipid A.

As described above, TMS methyl glycoside analysis revealed an unidentified component eluting 2 min prior to glucosamine. GLC-MS (CI) analysis of this TMS and N-acetylated TMS derivatives resulted in the mass spectra shown in FIGS. 4 and 5, respectively. Both the electron-impact (e.i.) and chemical ionization (c.i.) mass spectra of the TMS derivatives with and without N-acetylation are consistent with this component being the TMS methyl ester of 2-aminogluconic acid (GlcN-onic acid). These data were identical to those obtained from authentic 2-aminogluconic acid (Sigma Chemical Co., St. Louis, Mo.) Additionally, when the sample was subjected to mild methanolysis (methanolic 0.5M HCl, 2 h at 80° C.), reduction of the carboxymethyl group using $NaBD_4$, hydrolysis (2M trifluoroacetic acid (TFA), 1 h at 100° C.) and preparation of alditol acetates, the presence of the alditol acetate of glucosamine was found as expected. The mass spectrum of the resulting glucosaminitol alditol acetate gave ions at m/z 145 and 85, and 146 and 86. The former ions (i.e., m/z 145 and 85) result from one deuterium atom at C-1 indicating that the molecule giving rise to these ions is derived from glucosamine. The latter ions at m/z 146 and 86 result from two deuterium ions at C-1 indicating that this second molecule is derived from 2-aminogluconic acid. The relative intensities of the m/z 146 and 145 ions suggested that the glucosamine: 2-aminogluconate ratio was 1:1. Subsequently, this ratio was verified by GLC-MS analysis using authentic glucosamine and 2-aminogluconate to obtain accurate response factors.

Fatty acid analysis of the lipid A revealed the presence of β-hydroxymyristate, β-hydroxypalmitate, β-hydroxystearate, β-hydroxypentadecanoate, and 27-hydroxyoctaeosanoate (3-OH—$C_{14:0}$, 3-OH—$C_{15:0}$, 3-OH—$C_{16:0}$, 3-OH—$C_{18:0}$ and 27-OH—$C_{28:0}$, respectively). These fatty acids have been individually reported in this lipid A (5,8), as well as the lipid A from other *R. leguminosarum* strains (5). The composition of the lipid A is given in Table I. On a molar basis, a total of five fatty acid chains were present per mole of glucosamine. However, this number of fatty acyl residues is somewhat low since the methanolysis procedure used does not release the N-linked fatty acids quantitatively.

TABLE I

Comparison of *R. leguminosarum* lipid A.

| Component[a] | Mole Ratio |
|---|---|
| galacturonic acid | 1.21 |
| glucosamine | 1.00 |
| 2-aminogluconate | 0.92 |
| 3-OH—$C_{14:0}$ | 2.22 |
| 3-OH—$C_{15:0}$ | 0.17 |
| 3-OH—$C_{16:0}$ | 0.94 |
| 3-OH—$C_{18:0}$ | 0.51 |
| 27-OH—$C_{28:0}$ | 0.82 |

[a]Most lipid A preparations contained trace amounts of O-antigen and core region carbohydrates, including 3-O-methyl rhamnose, fucose, mannose and 2-keto-3-deoxy-octulosonic acid (Kdo). These trace components, as well as a small percentage of the galacturonic acid originating from the core region, could be removed from the lipid A preparations by extensive washing of the lipid A precipitate with water, followed by centrifugation.

Comparison of the total fatty acids, with those found after removal of the ester-linked fatty acids showed that β-hydroxypalmitate and β-hydroxystearate are exclusively amide-linked, while β-hydroxymyristate is both amide- and ester-linked, and β-hydroxypentadecanoate and 27-hydroxyoctacosanoate are exclusively esterlinked although the 27-hydroxyoctaeosanoate group is strongly believed to be located at O-5 of the 2-aminogluconate residue. However, the 27-hydroxyoctacosanoate group may also be at the O-3 or O-4 position of the 2-aminogluconate residue or at the O-3 position of the glucosamine residue. Nonetheless, there is only one 27-hydroxyoctaeosanoate group on any single lipid A analog of the present invention.

In addition to removal of the ester-linked fatty acids, methoxide treatment of β-hydroxy acyloxyacyl substituents results in the production of unsaturated fatty acids due to β-elimination (40). While this was observed for the lipid A from Salmonella (analyzed as a positive control), no such unsaturated fatty acids were produced from this Rhizobium lipid A. Thus, Rhizobium lipid A does not contain an acyloxy substituent that is esterified to a β-hydroxy fatty acid. The amide-linked fatty acids were also identified by mild methanolysis, trimethylsilylation and analysis by GC-MS. This procedure releases all ester-linked fatty acids, and cleaves the glycoside bonds, but does not release the amide-linked fatty acyl residues (4). This procedure resulted in the TMS methyl glycosides of three types of N-acylglcosamine residues; β-hydroxymyristylglucosamine, β-hydroxypalmitylglucosamine, and β-hydroxystearylghcosamine. This result demonstrates that this Rhizobium lipid A (as currently purified) is heterogeneous (or microheterogenous) with regard to the amide-linked fatty acyl residues. This is unlike the lipid A from enteric bacteria in which β-hydroxymyristate is the only amide-linked fatty acid.

Figures 6A, 6B, 6C:
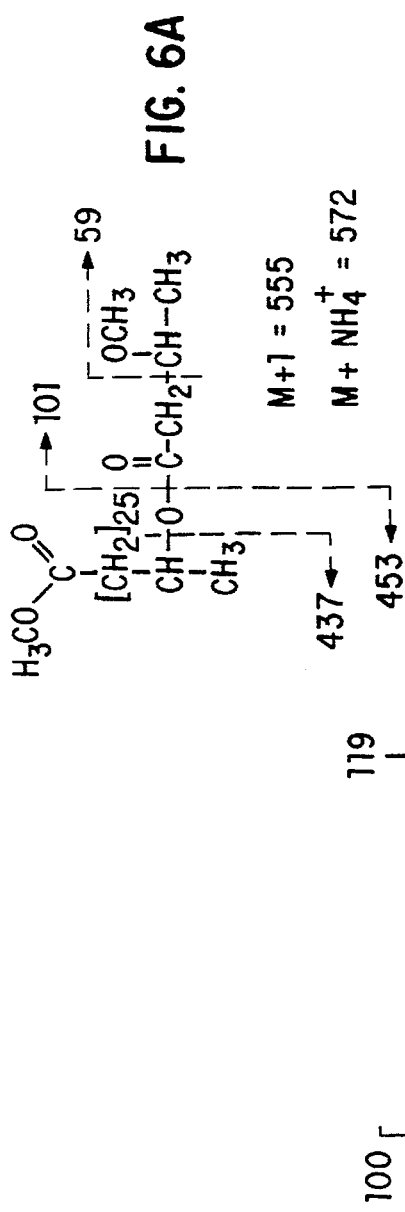
FIG. 6 shows the e.i.-m.s. (top) and c.i.-m.s. (bottom) spectra of the acyloxyacyl methyl ester released from *R. leguminosarum* bv. phaseoli CE3 lipid A by Kraska methylation.
Figure 6D:
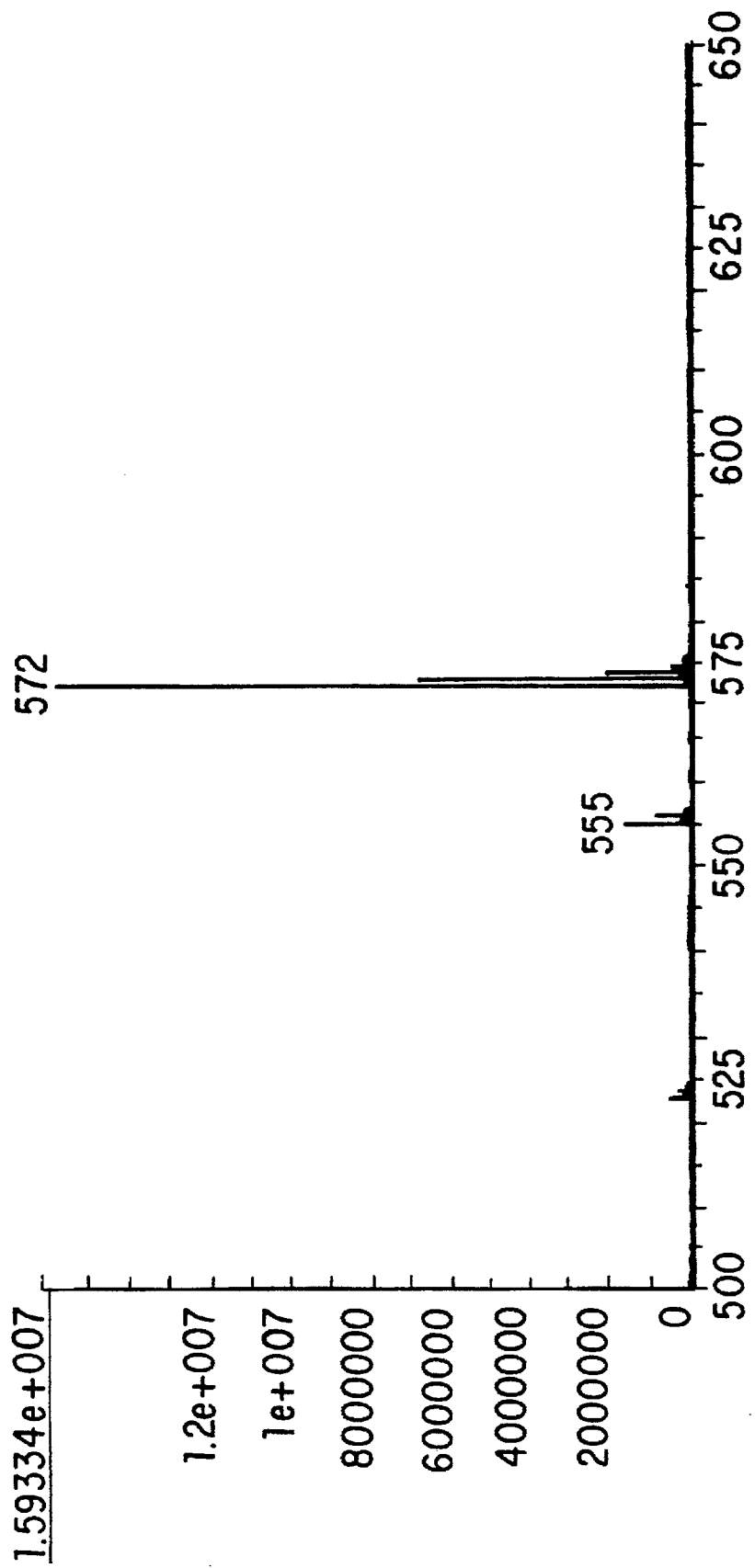

The Kraska methylation procedure was used to identify any amide-linked acyloxyacyl residues. This procedure resulted on only one acyloxyacyl residue; 27-(β-hydroxybutoxy)-octacosanoic acid. The electron-impact mass spectrum of the methyl ester of this residue is shown in FIG. 6. Since previous results suggested that 27-hydroxyoctaeosanoic acid was ester linked, this result suggests that this long chain fatty ester is cleaved by Kraska methylation.

Glycosyl Linkage Analysis

Permethylation, reduction of the carboxymethyl group of galacturonic acid, and preparation of alditol acetates resulted in a 1:1 ratio of terminally linked galacturonic acid and 4-O-substituted glucosamine. A partially methylated alditol acetate derivative of 2-aminogluconic acid was not observed. It is thought that this residue is labile and degraded during the methylation procedure. That the galacturonic acid was linked to O-4 of the glucosamine was verified by permethylation, β-elimination, and ethylation with conversion to alditol acetates. The partially methylated, ethylated alditol acetates were prepared and analyzed by GC-MS. A partially methylated, ethylated alditol acetate of glucosamine was observed in which the ethyl group was located at C-4; the mass spectrum showed primary fragments of m/z 217, 203, 175 and 159. Thus, the terminal galacturonosyl residue was linked to O-4 of the glucosaminosyl residue in the lipid A carbohydrate backbone.

Figure 14A:
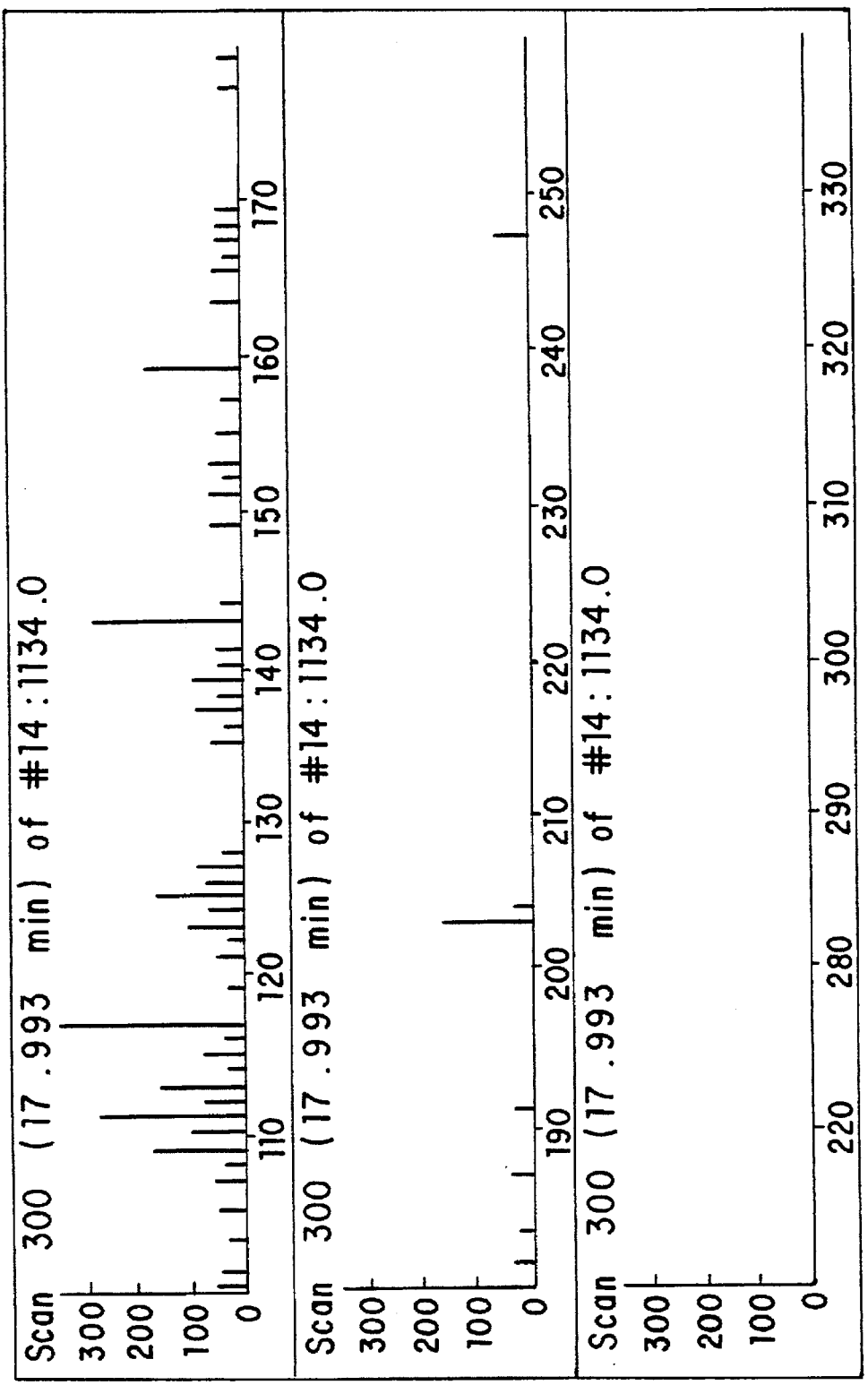
FIG. 14 shows the mass spectrum of the partially methylated/ethylated alditol acetate of the lipid A glucosamine residue after beta-elimination of the galacturonosyl residue from the permethylated lipid A of R. leguminosarum bv. phaseoli CE3 (A), or the LPS from strain CE309 (B), and after mild acid hydrolysis of the permethylated LPS from strain CE309 (C).
Figure 14B:
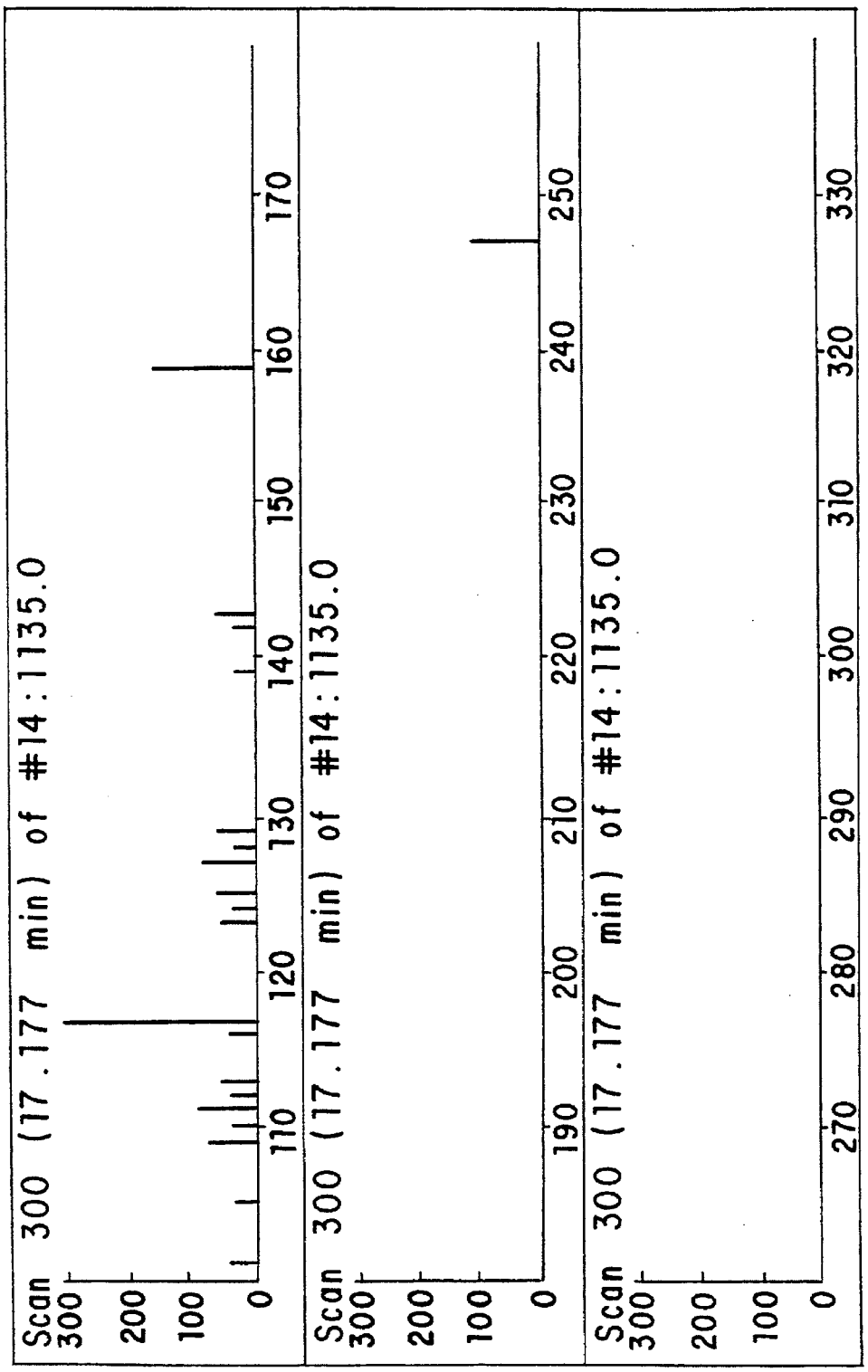

The site of attachment of the core oligosaccharide to the lipid A backbone was determined by methylation analysis of the intact LPS from a mutant of CE3, strain CE309. This mutant produces LPS which lacks the O-chain polysaccharide and has an altered core oligosaccharide (47). Methylation of this LPS showed that glucosamine was present as a 4,6-di-O-substituted residue (data not shown). Permethylation, followed by β-elimination, ethylation and alditol acetate derivatization resulted in N-acetyl-N-methyl-1,5,6-tri-O-acetyl-3-O-methyl-4-O-ethylglucosaminitol. The presence of a single ethyl group at O-4 of this derivative again indicates that the galaeturonosyl residue was "β-eliminated" from O-4 of the 4,6-linked glucosamine, suggesting that the core oligosaccharide must be linked to O-6 of this glucosaminosyl residue. The linkage of the core oligosaccharide to lipid A at this position was verified by ethylation of the permethylated, carboxymethyl reduced LPS after mild acid hydrolysis (0.2M TFA, 30 min at 70 °C.), conditions which selectively cleave the Kdo glycosidic bond. During this procedure, the newly exposed (due to mild acid hydrolysis) hydroxyl group on the lipid A backbone, becomes ethylated preparation and analysis of the partially methylated, ethylated alditol acetates resulted in N-acetyl-N-methyl-1,4,5-tri-O-acetyl-3-O-methyl-6-O-ethylglucosaminitol, FIG. 14B. The presence of the ethyl group at O-6 showed that this position had been occupied by a mild acid-labile group, presumably the Kdo residue of the core oligosaccharide, in the intact LPS.

The fatty acid substitution of the lipid A sugar backbone was determined by silica-catalyzed methylation (46) under neutral conditions, followed by carboxyl group reduction, and conversion to the alditol acetates. This procedure allows methylation of all hydroxyl groups that are not blocked by a fatty acyl or glycosyl residue. The resulting glucosamine derivative was methylated only at O-6, indicating that this residue was substituted at O-3 by a fatty acid ester. Numerous methylated derivatives of the galacturonosyl residue were also observed, presumably due to undermethylation. Derivatives with a methyl group at all possible locations (i.e. at O-2, O-3, and/or O-4) were present indicating that the galacturonosyl residue is not acylated.

Figure 15D:
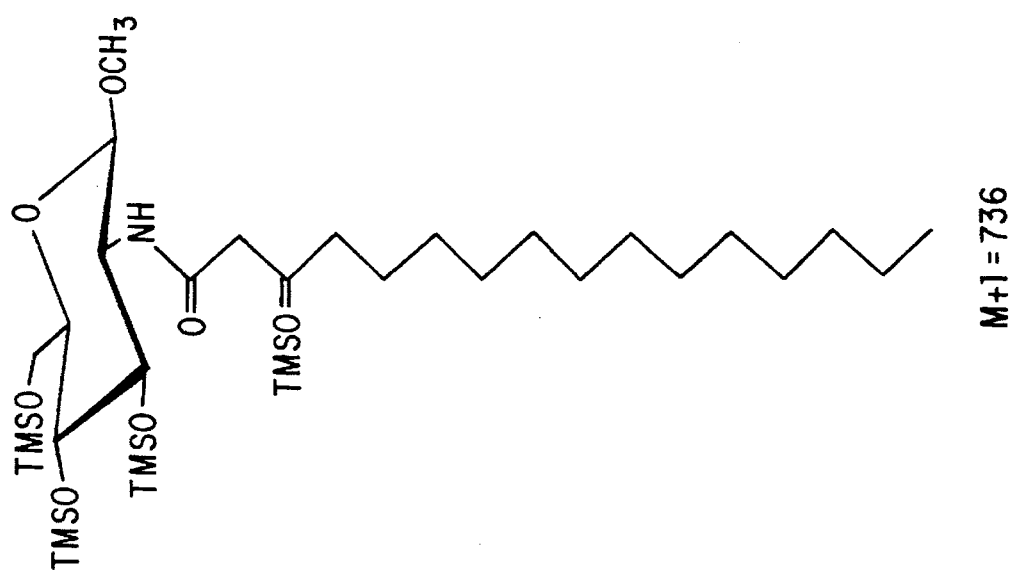
FIG. 15 shows the CI and EI mass spectra of the N-acyl TMS methyl glycosides from R. leguminosarum bv. phaseoli CE3 lipid A. (A, $GN-3-OH_{14:0}$; B, $GN-3-OH_{16:0}$; C, $GN-3-OH_{18:0}$).
Figure 15D:
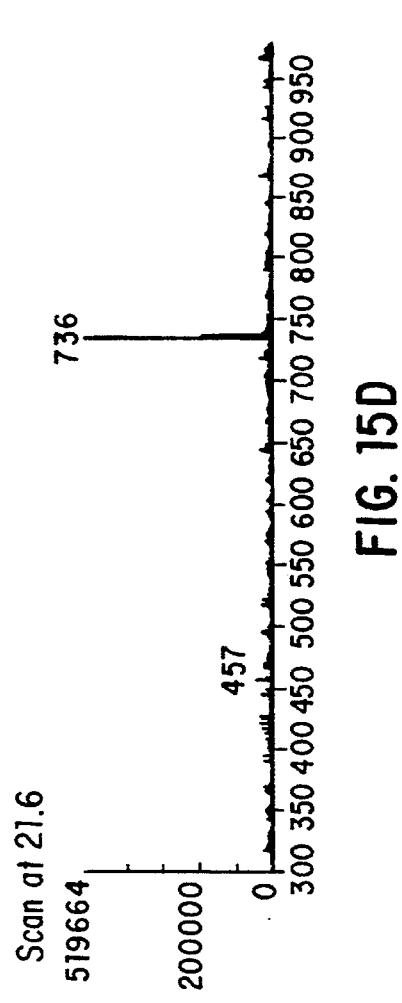
Figure 15E:
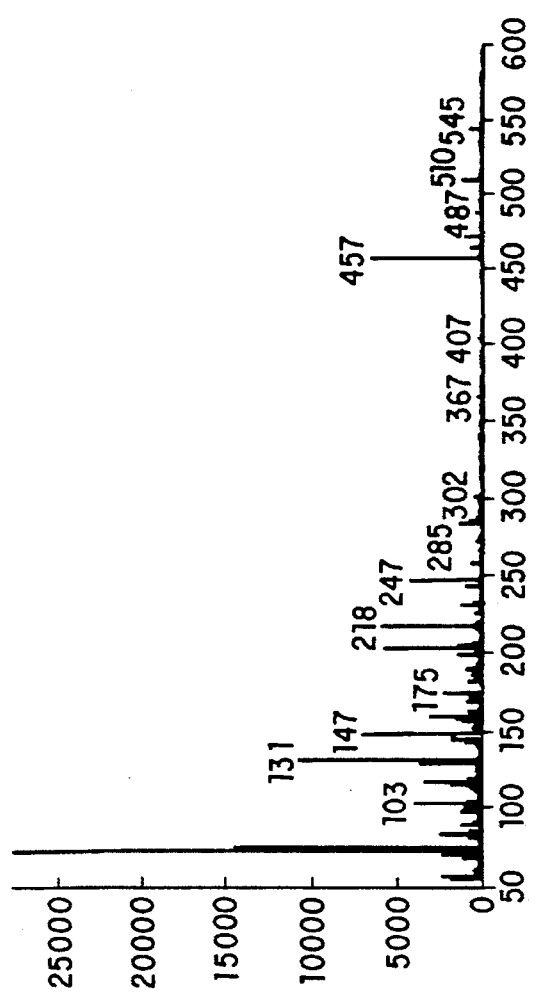

The amide-linked fatty acids in lipid A were investigated by mild methanolysis, trimethylsilylation and analysis by GLC-MS. This procedure releases all ester-linked fatty acids, and cleaves the glycosidic bonds, but does not release the amide-linked fatty acyl residues (4). The TMS methyl glycosides of three types of N-acyl glucosamine residues were observed: N-B-hydroxymyristylglucosamine (GlcN-[3-OH—$C_{14:0}$]), N-β-hydroxypalmitylglucosamine (GlcN-[3-OH—$C_{16:0}$]), and N-β-hydroxystearyglucosamine (GlcN-[3-OH—$C_{18:0}$]) present in a 1.00:0.28:0.07 ratio as determined from the TIC peak areas. These N-acyl glucosamine methyl glycosides were characterized by EI and CI mass spectrometry, and the spectra of the TMS methyl glycosides are shown in FIG. 15. The molecular ions (M+H)* were m/z 708, 736 and 764, observed for GlcN-[3-OH—$C_{14:0}$], GlcN-[3-OH—$C_{16:0}$], and GlcN-[3-OH—$C_{18:0}$], respectively. In the EI spectra, the characteristic fragment ions involve C-1, C-2 and C-3. The structures and origins of these fragment ions are consistent with those reported for other TMS N-acyl Glen methyl glycosides (48). The fragment ions involving C-2 and C-3 (i.e. m/z 429, 457 and 485 for GlcN-[3-OH—$C_{14:0}$], GlcN-[3-OH—$C_{16:0}$], and GlcN-[3-OH—$C_{18:0}$], respectively) indicate the nature of the fatty acid substitution at C-2. The expulsion of the acyl ketene ion results in formation of m/z 131. These results indicate that R. leguminosarum bv. phaseoli lipid A is heterogeneous with regard to the glucosamine N-acyl substituents, unlike the lipid A from enteric bacteria in which the only amide-linked fatty acid is 3-OH—$C_{14:0}$.

Kraska methylation was performed in an attempt to identify any amide-linked acyloxyacyl residues. This procedure resulted in only one acyloxyacyl residue; its mass spectrum, FIG. 6, is consistent with 27-O-(g-hydroxybutoxy)-$C_{28:0}$. Analysis by GLC-MS (CI) gave an (M+NH$_4$)$^+$ion of m/z 572. The EI spectrum shows ions of m/z 59 and 101, which are consistent with a β-hydroxybutyrate substituent at the 27-hydroxy position of the long chain fatty acid. When Kraska methylation was carried out in the presence of trideuteriomethyl iodide these ions shifted to m/z 62 and 104, respectively, also consistent with trideuteriomethylation of a β-hydroxybutyric acid substituent. This acyloxyacyl residue was subjected to complete methanolysis followed by trimethylsilylation of fatty acid methyl esters. Only 27-O-TMS-$C_{28:0}$ was detected, showing that the 27-hydroxy group was not methylated by the Kraska methylation due to its substitution, presumably by β-hydroxybutyric acid. The TMS methyl ester of β-hydroxybutyric acid is very volatile and was not observed, presumably due to its loss during sample preparation. Alkaline cleavage of O-ester linkages, described below, showed that the 27-OH—$C_{28:0}$ is ester linked, not amide linked to the lipid A backbone suggesting that this long chain fatty ester, but not the other ester-linked fatty acids, is cleaved by Kraska methylation.

De-O-Acylation of Lipid A

Figure 16A:
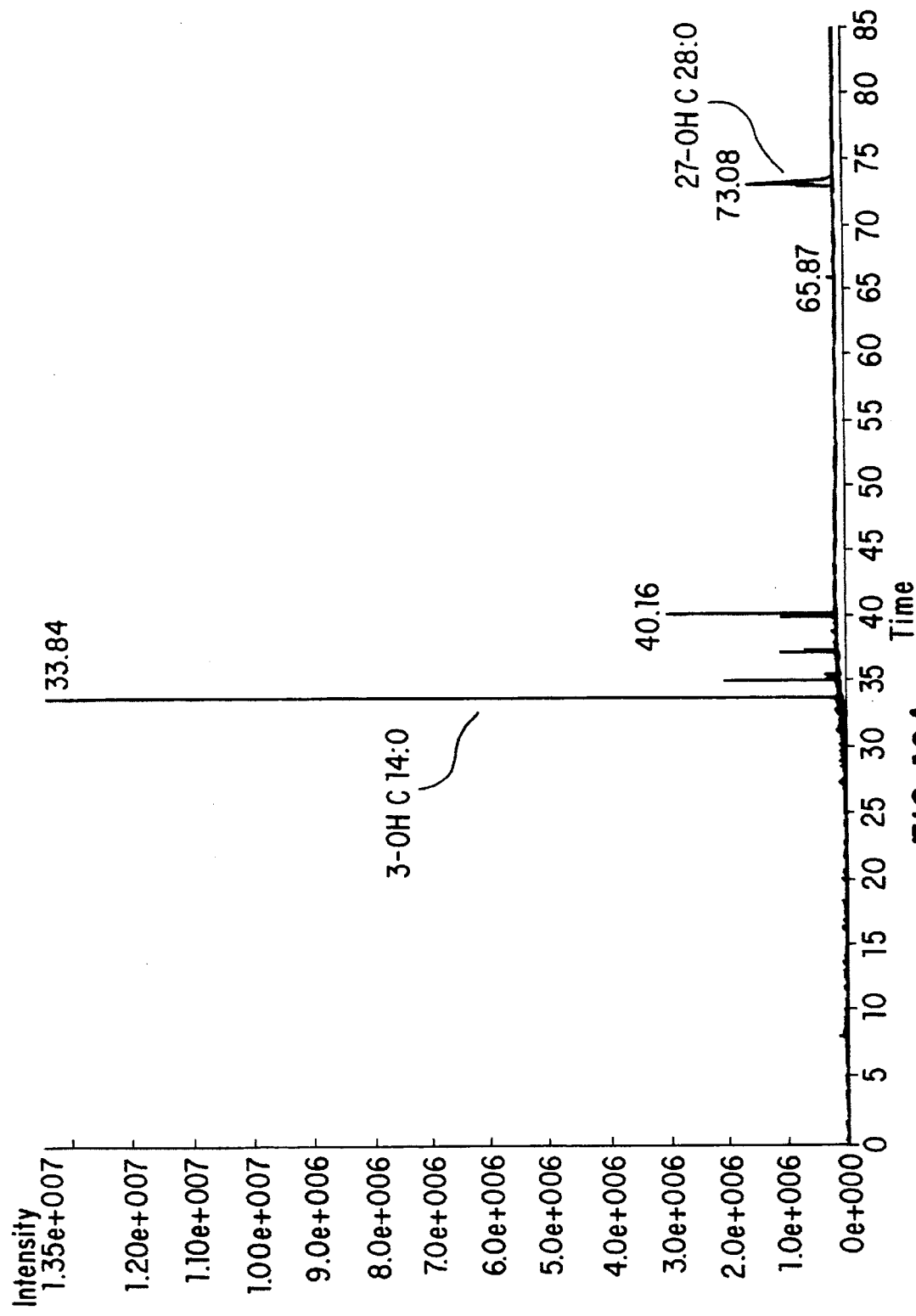
FIG. 16 shows a GLC profile of the fatty acids recovered during de-O-acylation of R. leguminosarum bv. phaseoli CE3 lipid A.
Figure 16B:
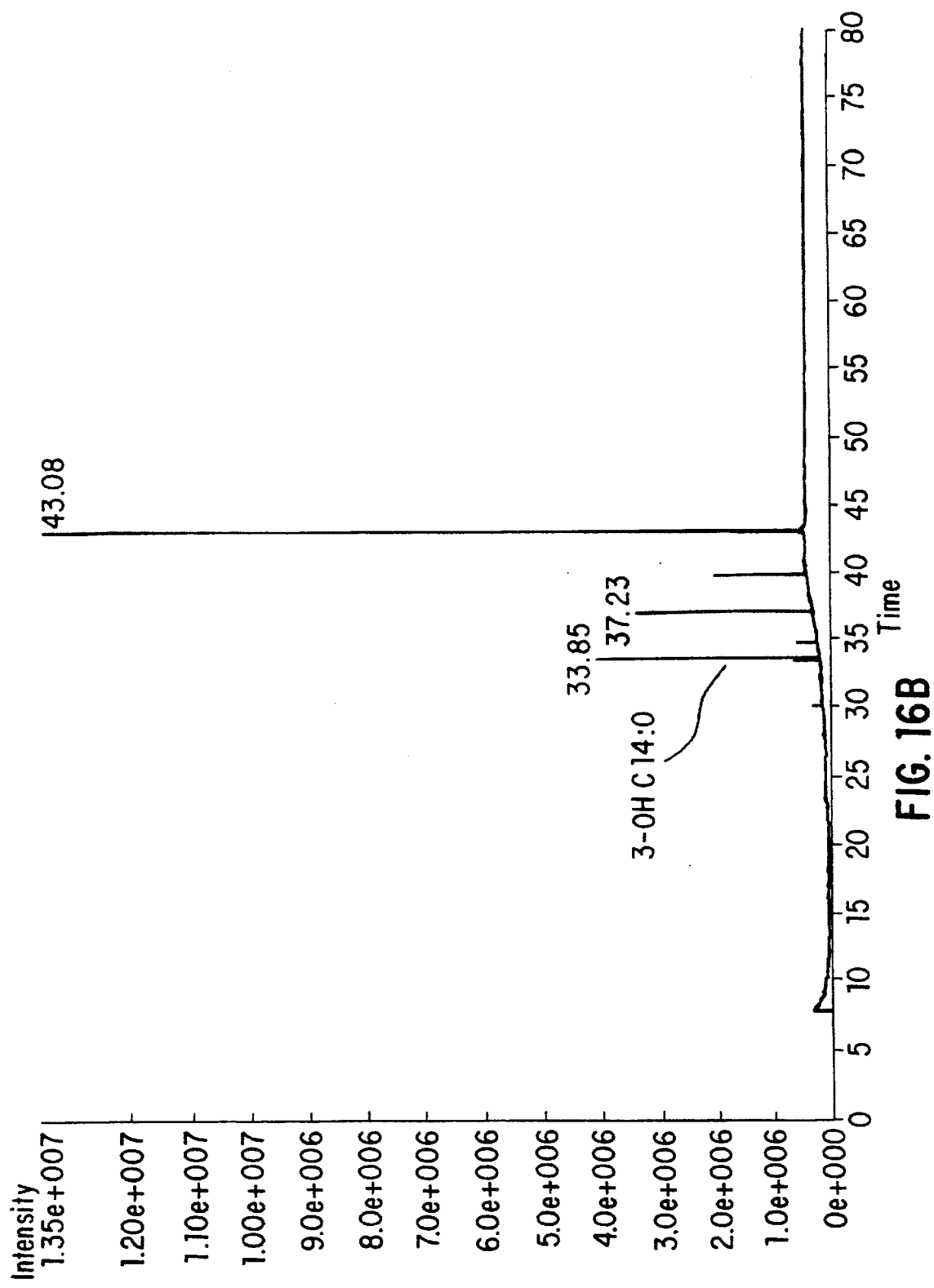

De-O-acylation of the lipid A yielded a methanolic supernatant containing released fatty acids and a precipitate consisting of the de-O-esterified lipid A. Analysis of the supernatant by trimethylsilylation and GLC-MS showed that it was devoid of carbohydrate but contained the free fatty acids: 3-OH—$C_{14:0}$, 3-OH—$C_{15:0}$, 3-OH—$C_{16:0}$, 3-OH—$C_{18:0}$, and 27-OH—$C_{28:0}$. Total fatty acid analysis (4M TFA, 4 h, 100 ° C.) of the precipitated de-O-acyl lipid A revealed it was composed of only three fatty acids, 3-OH—$C_{14:0}$, 3-OH—$C_{16:0}$, and 3-OH—$C_{18:0}$, and confirms that these are the amide-linked fatty acids in the lipid A molecule. The results further show that a portion of the 3-OH—$C_{14:0}$, 3-OH—$C_{16:0}$, and 3-OH—$C_{18:0}$ are also attached as O-esters, while essentially all of the 27-OH—$C_{28:0}$ and 3-OH—$C_{15:0}$ were released by sodium methoxide and are, therefore, exclusively esterlinked. The relative amounts of ester- and amide-linked fatty acids are summarized in Table II, and GLC profiles of the fatty acids recovered during de-O-acylation are shown in FIG. 16. If acyloxyacyl substituents involving β-hydroxy fatty acids were present, methoxide treatment would have resulted in the production of unsaturated fatty acids due to β-elimination (40). While this was observed for the lipid A from Salmonella (analyzed as a positive control), no such unsaturated fatty acids were produced from this Rhizobium lipid A. Thus, Rhizobium lipid A does not contain acyloxyacyl residues involving β-hydroxy fatty acids.

TABLE II

Recovery of Fatty Acids During de-O-acylation

| Component | ester-linked[a] nmole | % | amide linked[b] nmole | % | nmole |
|---|---|---|---|---|---|
| 3-OH—$C_{14:0}$ | 831.8 | 67.6 | 399.2 | 32.4 | 1231.0 |
| 3-OH—$C_{15:0}$ | 106.6 | 100.0 | trace | trace | 106.6 |
| 3-OH—$C_{16:0}$ | 111.1 | 27.0 | 299.7 | 73.0 | 410.8 |
| 3-OH—$C_{18:0}$ | 67.4 | 28.0 | 176.1 | 72.0 | 243.5 |
| 27-OH—$C_{28:0}$ | 436.2 | 100.0 | 0 | 0 | 436.2 |

Figure 17:
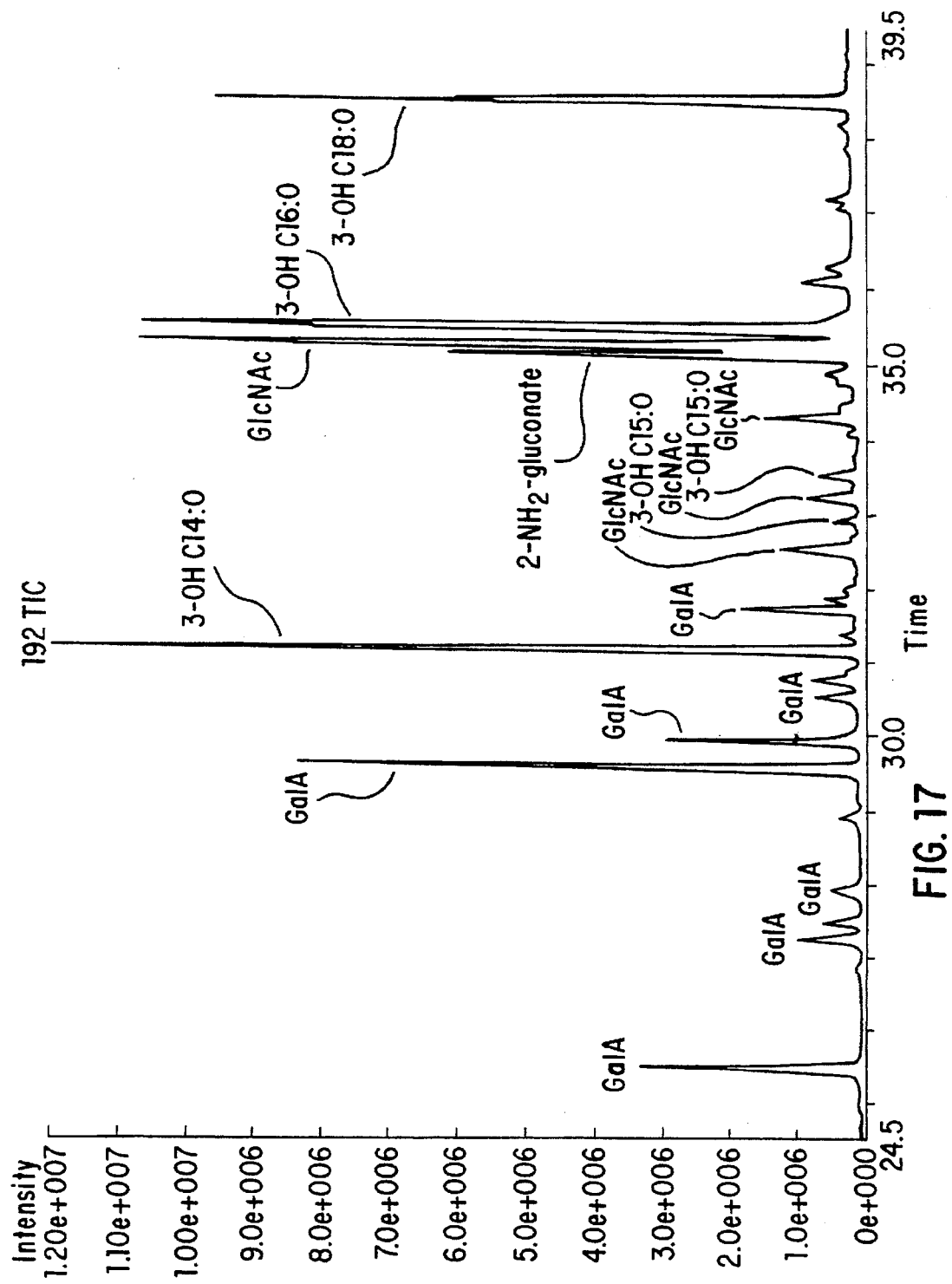
FIG. 17 shows a GLC profile showing the glycosyl and fatty acid composition of the de-O-acylated lipid A from R. leguminosarum bv. phaseoli CE3.

[a]Fatty acids released from lipid A by 0.5 M sodium methoxide in CHCl₃/MeOH
[b]Fatty acids released from the de-O-acylated lipid A using 4 M trifluoroacetic acid In a separate analysis, a portion of the de-O-acylated lipid A was subjected to total methanolysis, N-acetylation, and trimethylsilylation with GLC-MS analysis of the resulting derivatives (FIG. 17). In addition to the fatty acids described above, the carbohydrate components were identified as the TMS-methylglycosides of galacturonic acid and N-acetylglucosamine, and the methyl ester of N-acetyl-2-aminogluconic acid. Using response factors measured for authentic standards the calculated mole ratios were 1.00:0.82:0.72, respectively.

Mild methanolysis of the de-O-acyl lipid A followed by trimethylsilylation and GLC-MS analysis confirmed the presence of three N-acylglucosamine derivatives in a ratio consistent with those observed for the intact lipid A: (GlcN-[3—OH—$C_{14:0}$], GlcN-[3-OH—$C_{6:0}$], and GlcN-[3-OH—$C_{18:0}$], 1.00:0.26:0.13). The results confirm the data described above, that the 3-hydroxy 14, 16, and 18 carbon chain fatty acids are amide-linked, and that there is heterogeneity in the amide-linked fatty acids of Rhizobium lipid A.

N-acyl TMS derivatives of 2-aminogluconic acid were not observed, presumably due to the relatively high degree of acid-lability of N-acyl substituents on this compound. A comparison of the rates of methanolysis for authentic N-acetylglucosamine and N-acetyl-2-aminogluconate shows that after 1 hour at 80° C. and 10 percent of the N-acetyl group is cleaved from GltNAc, whereas essentially 100 percent of the N-acetyl group is removed from N-acetylgluconate.

Analysis of the Hydrazinolysis Product by FAB-MS and NMR

After hydrazinolysis of R. leguminosarum lipid A in anhydrous hydrazine followed by N-acetylation, the resulting product was analyzed by both positive FAB-MS and NMR. Positive FAB-MS shows a molecular ion ((M+H)⁺) of m/z 655 with a major fragment ion at m/z 436. This fragmentation pattern is consistent with a trisaccharide consisting of an N-acetylated hyrazide of galacturonic acid, an N-acetylated glucosamine residue, and an N-acetylated 2-aminogluconolactone residue. The fragment ion, m/z 436, is due to the N-acetylated GalA(hyrazide)-GlcNAc disaccharide component of this trisaccharide. The data are consistent with the methylation results above which show that the galacturonosyl residue is terminally linked to glucosamine in this lipid A, and that the glucosamine residue is, in turn, linked to 2-aminogluconic acid. The linkage of the 2-aminogluconic acid is under investigation. This residue is particularly labile to methylation procedures. However, it is reasonably certain that the precursor to this lipid A contains 6-linked glucosamine at this position rather than 2-aminogluconate, and that this glucosamine residue is later converted to 2-aminogluconate. Thus, the 2-aminogluconate residue can be linked at C-6. In addition, the linkage also can occur at the C-3 or C-4 position of 2-aminogluconic acid and these embodiments are specifically contemplated herein.

Figure 7:
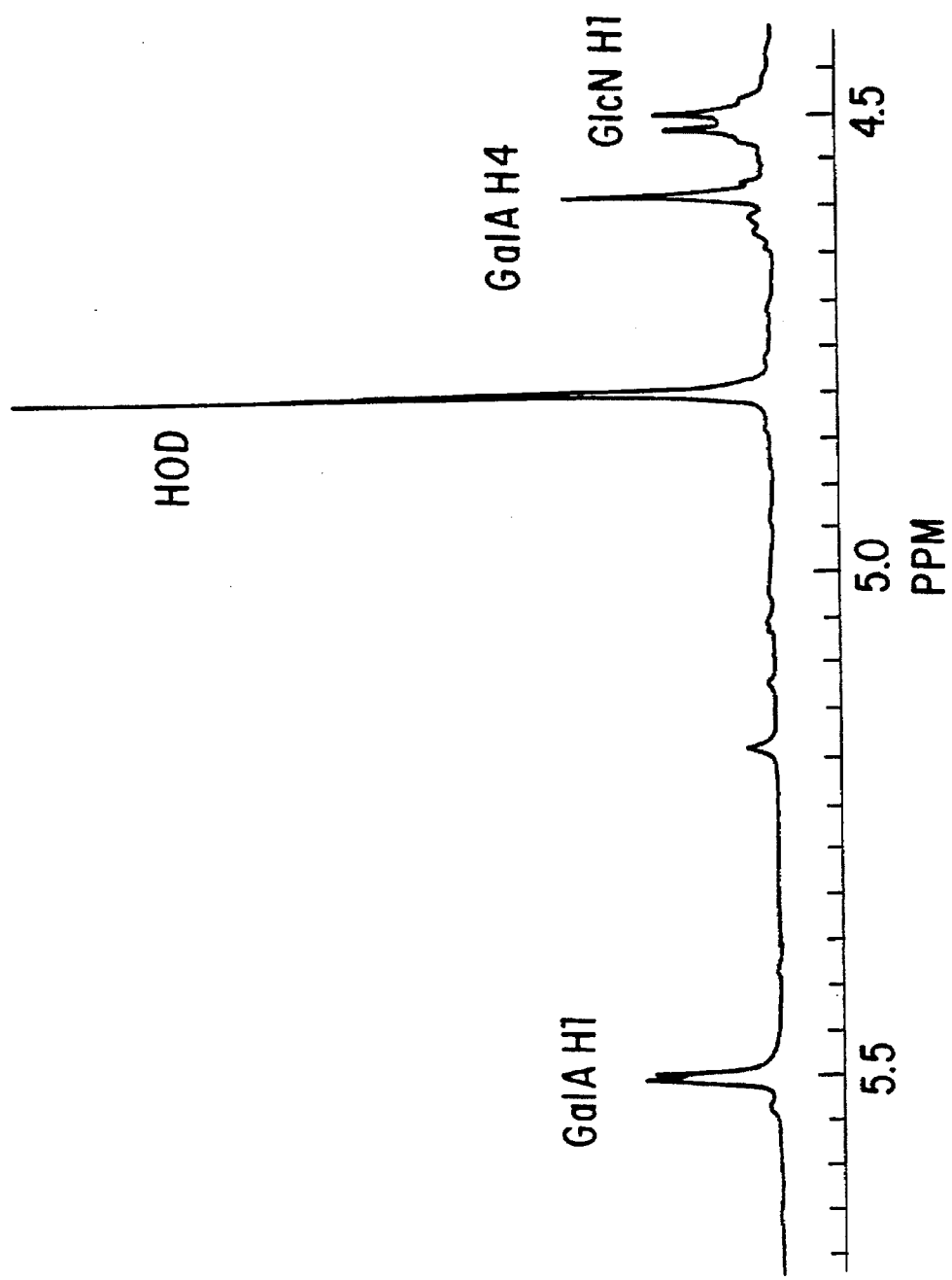
FIG. 7 shows the NMR spectrum, showing the anomeric region, of the N-acetylated hydrazinolysis product of the lipid A from *R. leguminosarum*. Gala H1, the anomeric proton of galacturonic acid; Glen H1, the anomeric proton of glucosamine.

NMR analysis of the hydrazinolysis product, FIG. 7, shows two anomeric resonances. The resonance at d 5.55 ($J_{12}$=3.4 Hz) is consistent with H-1 of an a-linked galacturonosyl residue. The resonance at d 4.51 ($J_{12}$=8.6 Hz) is consistent with H-1 of a β-linked glucosamine residue. The resonance at about d 4.59 with a small coupling constant can be assigned to the H-4 of the galacturonosyl residue. These results show that the Gala and GlcN residues in this trisaccharide are α- and β-linked, respectively.

FAB-MS Analysis of De-O-Acylated Lipid A

Figure 8A:
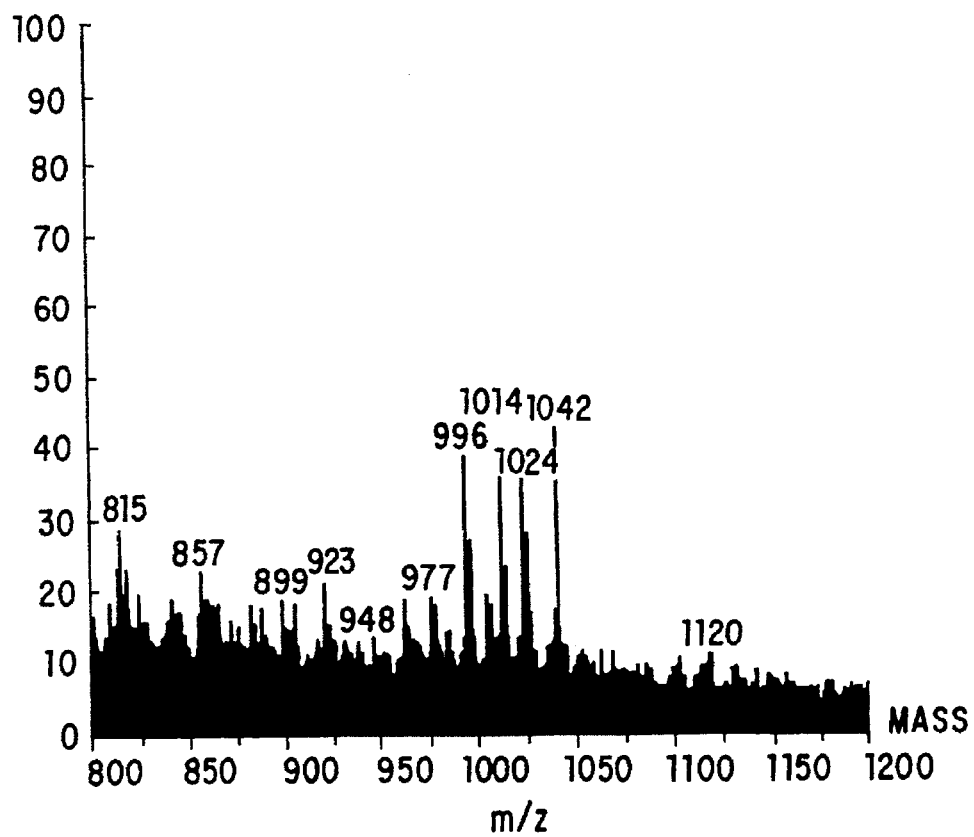
FIG. 8 shows the FAB-MS spectrum (top) of de-O-acylated lipid A from *R. leguminosarum* bv. phaseoli. The bottom panel shows the possible combinations of amide linked fatty acyl substituents that would give rise to the molecular ions observed in the FAB-MS spectrum. Both the acid and lactone forms of the 2-aminogluconate are presumably present in the FAB-MS spectrum.
Figure 8B:
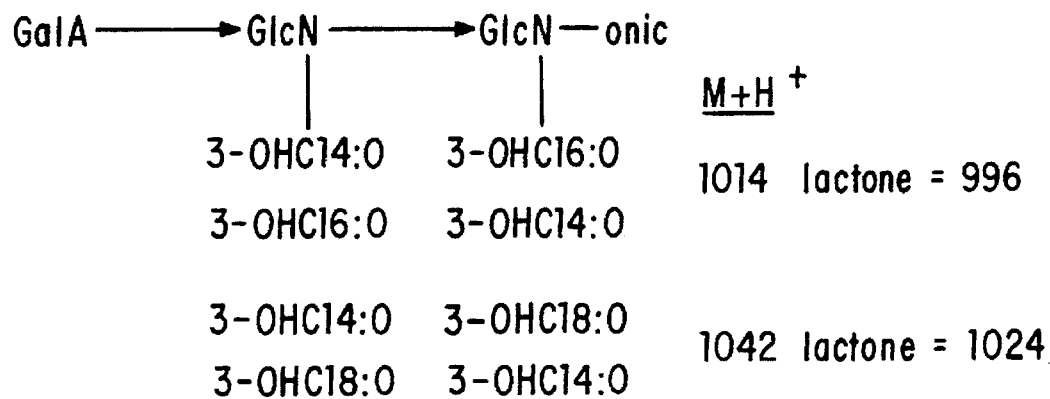

A portion of the lipid A was de-O-acylated with methoxide (40). Composition analysis of the resulting product shows the presence of galacturonic acid, glucosamine, 2-aminogluconic acid, β-hydroxymyristate, β-hydroxypalmitate, and β-hydroxystearate. The FAB-MS spectrum is shown in FIG. 8. The molecular ions are consistent with the strums shown in FIG. 8. Both acid and lactone versions of the molecule are present. The data also verify the heterogeneity occurring in the N-fatty acyl residues. Two combinations are possible: β-hydroxymyristyl with β-hydroxypalmityl, and β-hydroxymyristyl with β-hydroxystearyl substituents. Since it is known (4) that all three fatty acids can be present on the glucosamine residue, this result implies that there is equal heterogeneity in the acylation of the 2-aminogluconic acid residue.

Summary of Structural Analysis

Figure 1:
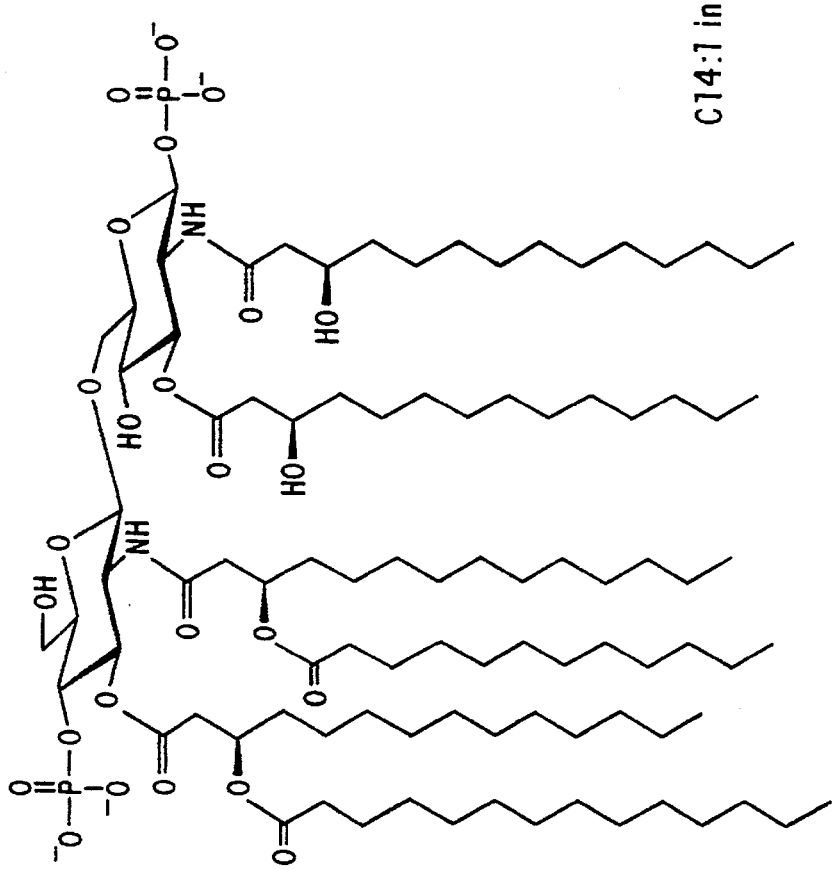
FIG. 1 shows the structure of the lipid A from *E. coli*.
Figure 3:
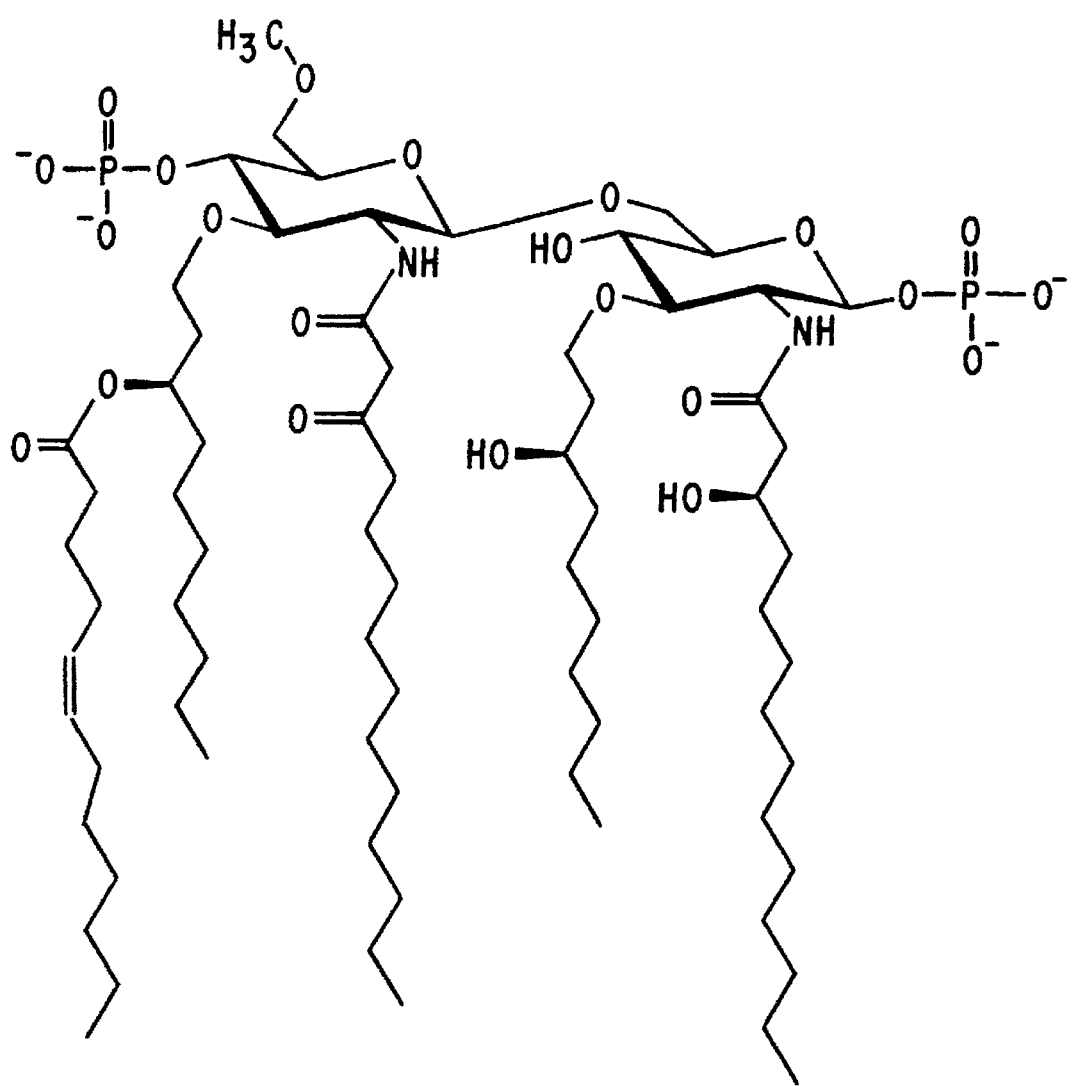
FIG. 3 shows the structure of the lipid A antagonist synthesized by Chris et al., at Eisai.
Figure 4A:
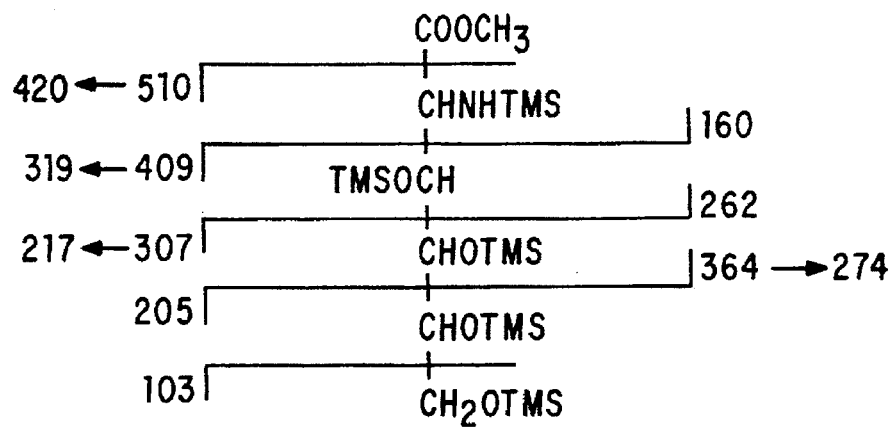
FIG. 4 shows the e.i.-ms.s. (panel A) and c.i.m.s. (panel B) spectra of the TMS derivative of methyl 2-aminogluconate from *R. leguminosarum* bv. phaseoli CE3 lipid A.
Figure 4B:
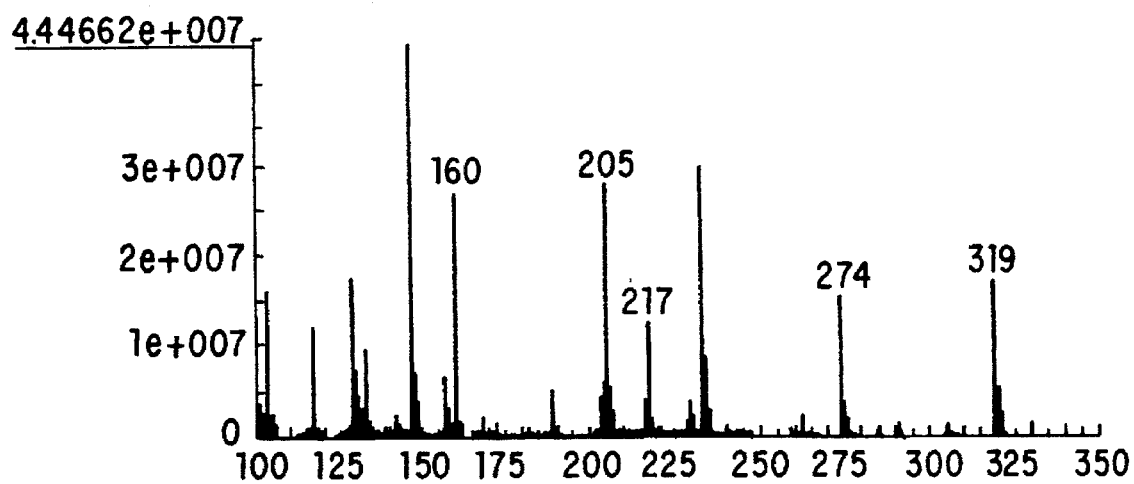
Figure 4C:
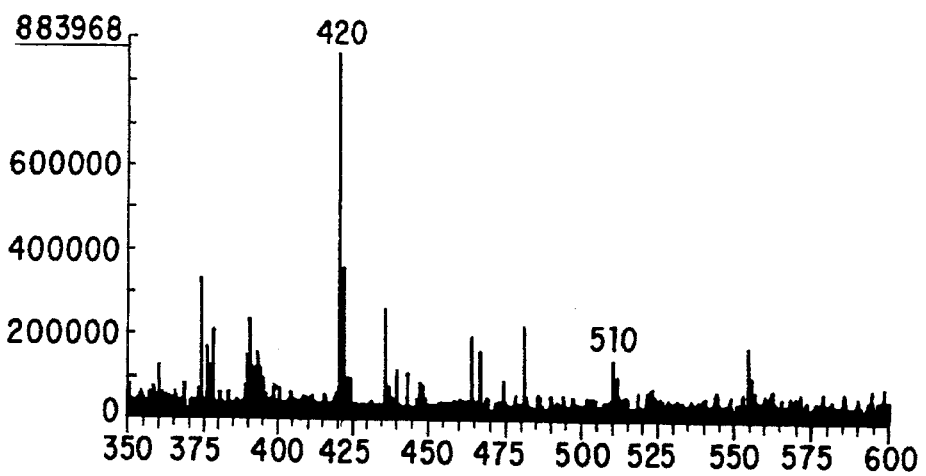
Figure 4D:
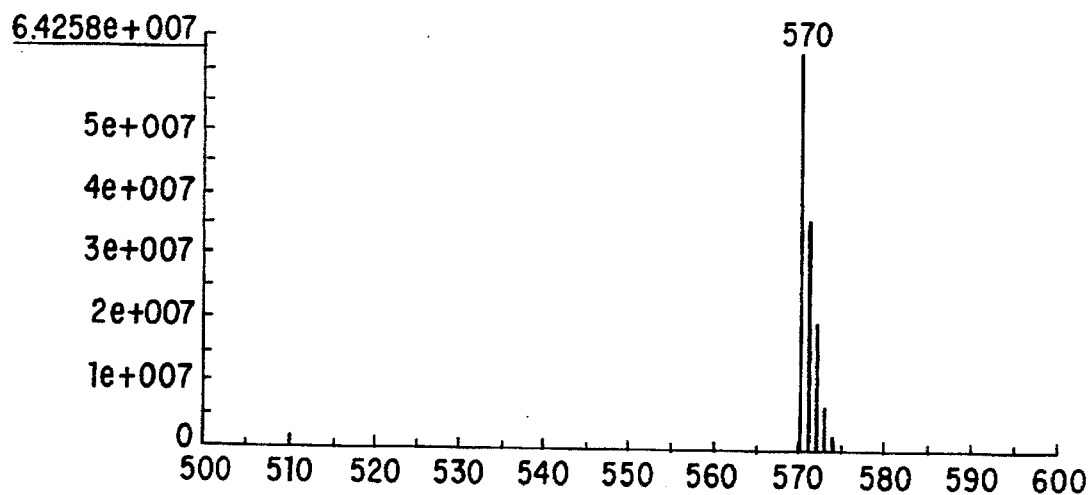
Figure 9B:
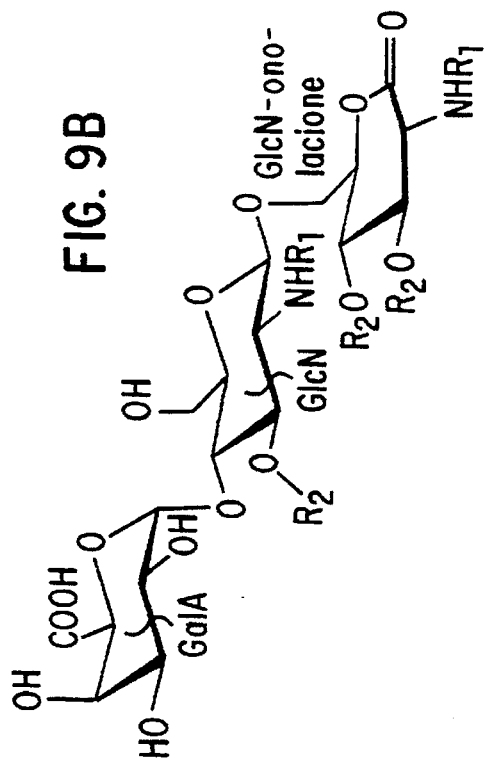
FIG. 9 shows a summary of the acid and lactone *R. leguminosarum* bv. phaseoli CE3 lipid A structures. $R_1$ and $R_2$ can be any of the designated fatty acyl substituents, however R1 must have the fatty acyl combinations shown in FIG. 8.
Figure 9A:
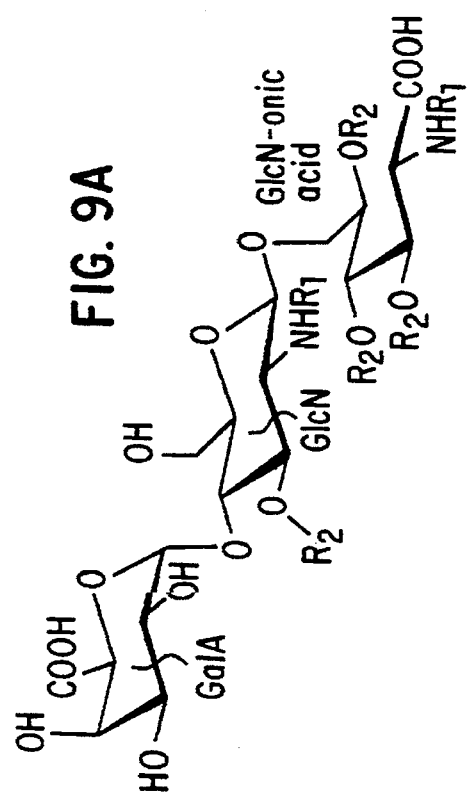

All of the above data support the structures shown in FIG. 9 for the lipid A from R. leguminosarum. For comparison, the structure of E. coli lipid A is shown in FIG. 1. The Rhizobium lipid A differs from that of E. coli in several aspects:

1. Them is no phosphate, and a Gala residue, not phosphate, is present at the 4' position of the glucosamine residue.

2. The reducing-end consists of a 2-aminogluconate residue instead of glucosamine.
3. There is heterogeneity in the N-fatty acylation pattern.
4. There are no ester- or amide-linked acyloxyacyl substituents located on any of the β-hydroxy fatty acids.
5. The very long chain fatty acid, 27-hydroxyoctacosanoate, is found in Rhizobium, but not *E. coli*, lipid A and can contain β-hydroxybutoxy group as an acyloxy substituent.

FIG. 9B also shows structures that are present due to the lactone versions (GlcN-ono-lactone) of the β-2-aminogluconate residue of this lipid A. These lactone versions are likely formed during the isolation of this lipid A. However, these novel lactone versions, based on their similarity to the natural lipid A, would be expected by one skilled in the art to provoke similar systemic responses in subjects.

Comparison Of *Rhizobium* species

Composition analysis of lipid A from several other strains of *R. leguminosarum* bv. viciae, trifolii and phaseoli suggests that they may be identical in structure. The lipid A from strains representing all three biovars contains the same fatty acyl residues as those present in the *R. leguminosarum* bv. phaseoli lipid A described here; however, some quantitative variations are noted (5). Additionally, these lipid As all lack phosphate, and contain galacturonic acid, glucosamine (5) and 2-aminogluconate. It has also been shown that the core oligosaccharides released by mild acid hydrolysis of the LPS from various strains of these three biovars have identical structures (47, 49–51). Thus, it is likely that the core oligosaccharide-lipid A regions of other *R. leguminosarum* LPSs have a common structure.

The lipid A from *R. leguminosarum* bv. trifolii ANU843, is reported not to contain glucosamine or phosphate, but consists of 2-aminoglucuronic acid which is N-acylated 27-OH-$C_{28:0}$, and 3-O-acylated with β-hydroxymyristic acid (53). However, composition analysis of the lipid A from *R. leguminosarum* bv. trifolii ANU843 revealed no evidence for this structure. The lipid A from this strain, however, was determined to be identical in structure to that described herein for *R. leguminosarum* bv. phaseoli CE3.

There is a partial explanation for the discrepancies in these data. First, the procedures described in the prior report (53) to determine glycosyl composition may not have released the N-acyl group from the glucosamine residue, and, therefore, may explain the apparent lack of glucosamine. Second, the reported (53) increase in the mount of glucosamine after mild methanolysis and $NaBH_4$ reduction may have been the result of reducing the 2-aminogluconosyl residue, and not due to the presence of 2-aminoglucuronic acid. It is surprising that these workers (53) did not observe galacturonic acid in their lipid A preparation, or their observation that 27-OH-$C_{28:0}$ is amide linked, instead of ester linked.

The second report describes the structure of the lipid A from an *R. trifolii* strain isolated in Poland as consisting of the more common β-1,6-glucosamine disaccharide backbone which is bis-phosphorylated at positions 1 and 4' (52). There is no evidence of such a structure in any of the *R. leguminosarum* strains examined. However, strains isolated from Poland have not yet been examined. Recently, the *R. leguminosarum* bv. phaseoli strain was re-classified (based on 16S RNA homology studies) as *R. etli* (54). Thus, it is possible that the *R. trifolii* strain isolated in Poland represents a different *Rhizobium* species than the *R. leguminosarum* strains disclosed herein. Homology studies, using 16S RNA, would help clarify the relationship of these *R. leguminosarum* strains to the Polish *R. trifolii* strain.

In the case of the lipid A from enteric bacteria, the phosphate substituents of the 1,4'-bisphosphorylated β-1,6-linked glucosamine disaccharide are crucial for the viability of the bacterium, and, together with the type of fatty acylation pattern, determine the immunostimulatory and toxic properties of the lipid A molecule (31,55). The carboxy groups of the 2-aminogluconic and galacturonic acid residues may functionally substitute for these phosphate groups. In addition to the lack of phosphate, the Rhizobiura lipid A of the present invention has an altered fatty acylation pattern when compared with the lipid A from enteric bacteria.

EXAMPLE 2

The stimulation of IL-1 and IL-6 by *Rhizobium leguminosarum* lipid A
The Production of Interleukins (IL) 1 and 6

The ability of the novel lipid A discussed herein to stimulate the immune system, i.e. the production of IL-1 and IL-6, was determined with an in vitro assay, using mononuclear cells (MNC). The procedure was performed in the laboratory of Dr. Ernst Rietschel, Forschungsinstitut fur Medizin, Borstel, Germany utilizing procedures previously described (21,22).

Figure 10:
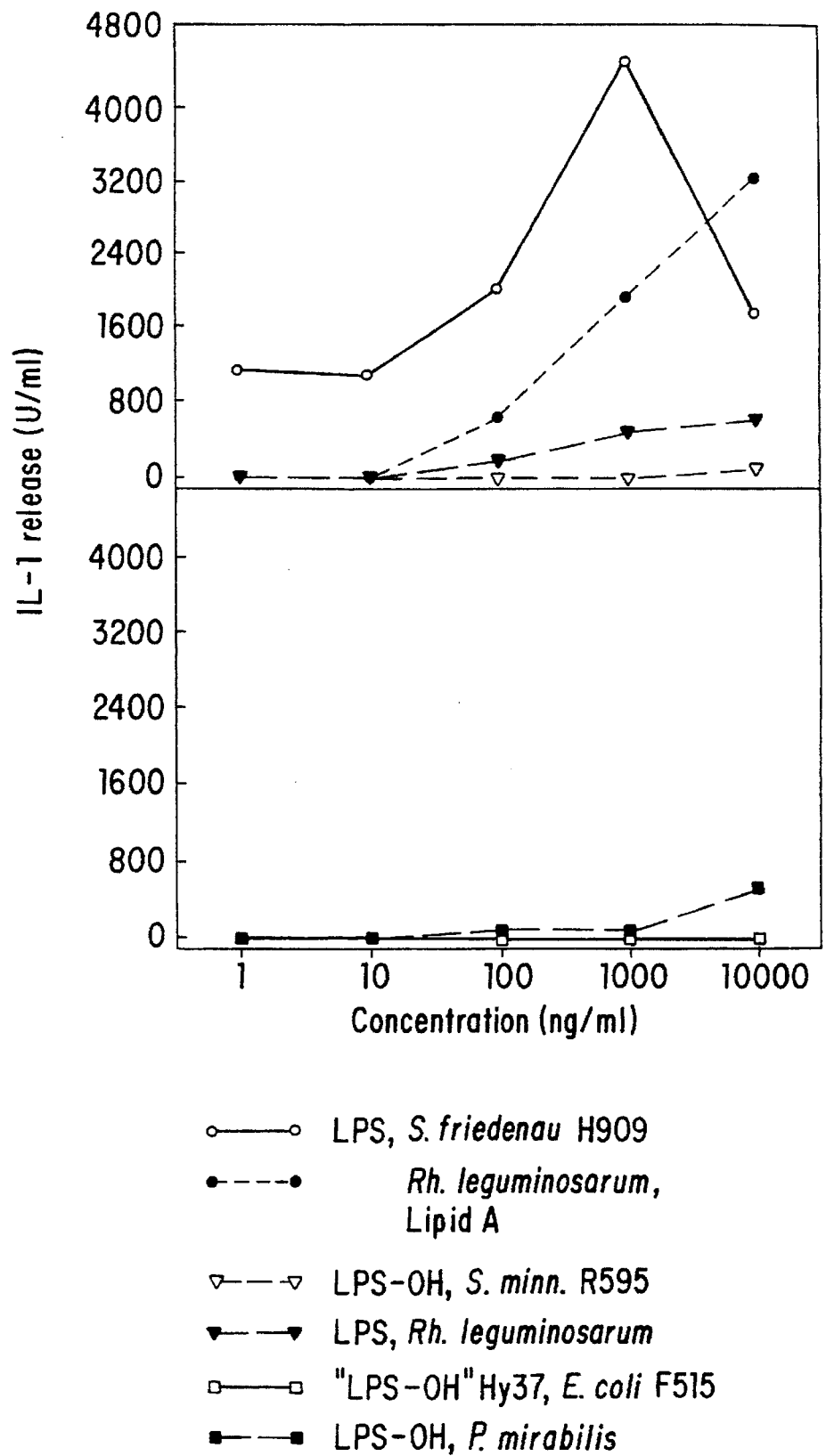
FIG. 10 shows the induction of MNC to produce IL-1 by various lipid A molecules. The LPS-OH samples are de-O-acylated lipid A from the indicated organisms, and are used as negative controls. The *S. friedenau* LPS is a positive control.
Figure 11:
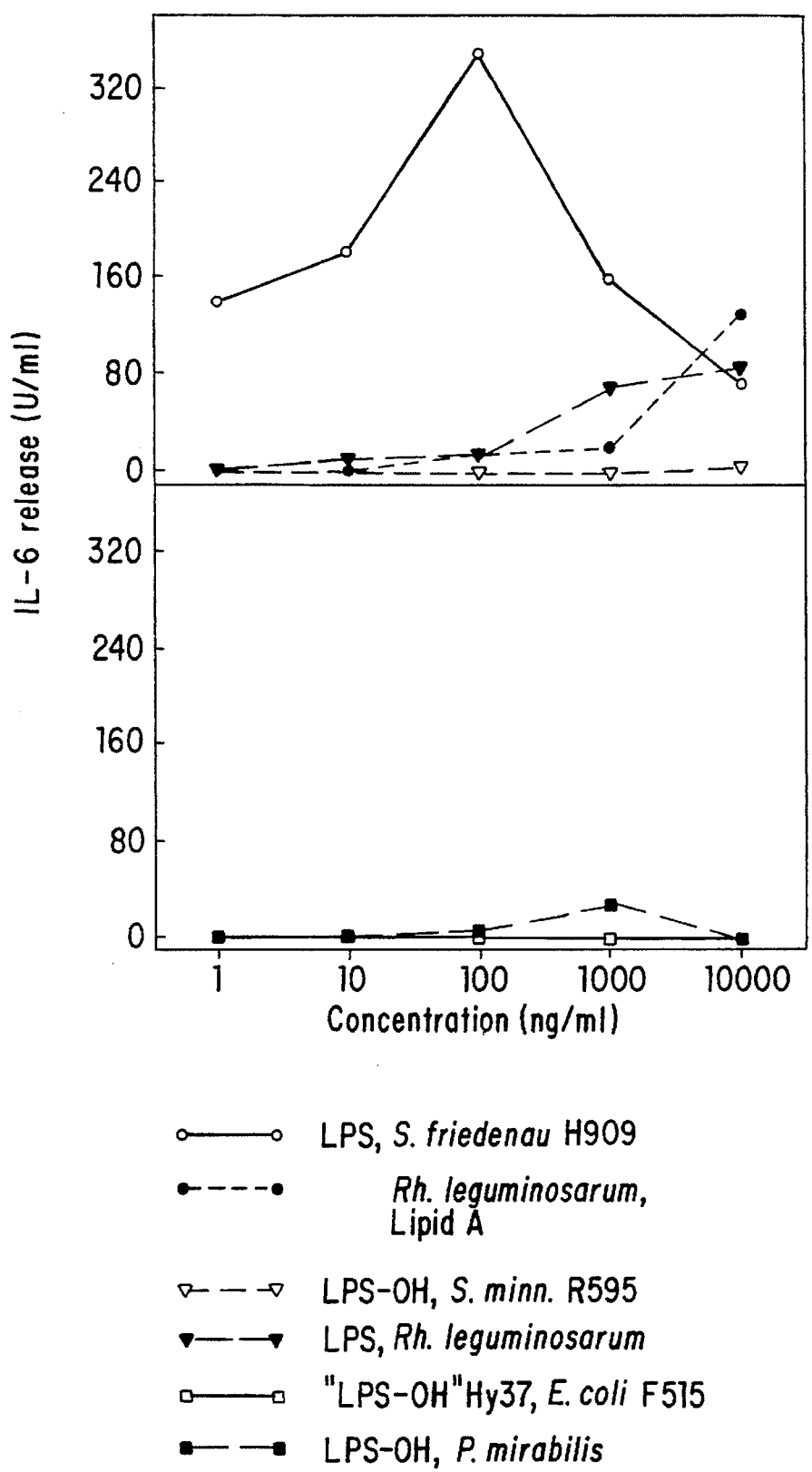
FIG. 11 shows the induction of MNC to produce IL-6 by various lipid A molecules. The lipid A samples are as described for FIG. 10.
Figure 12:
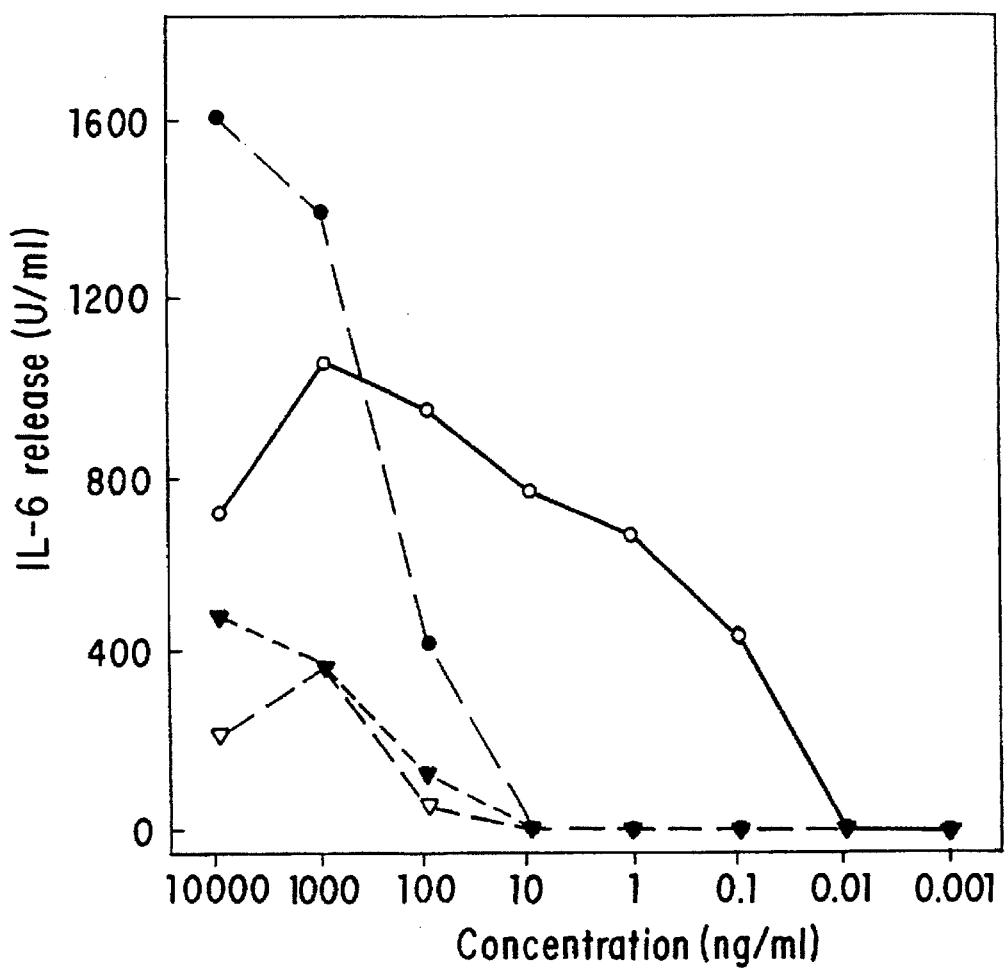
FIG. 12 shows the induction of MNC to produce IL-6 by various lipid A molecules. The concentration range of the various lipid A samples is different from that for FIG. 11. The lipid A samples are as defined in FIG. 10.
Figure 13B:
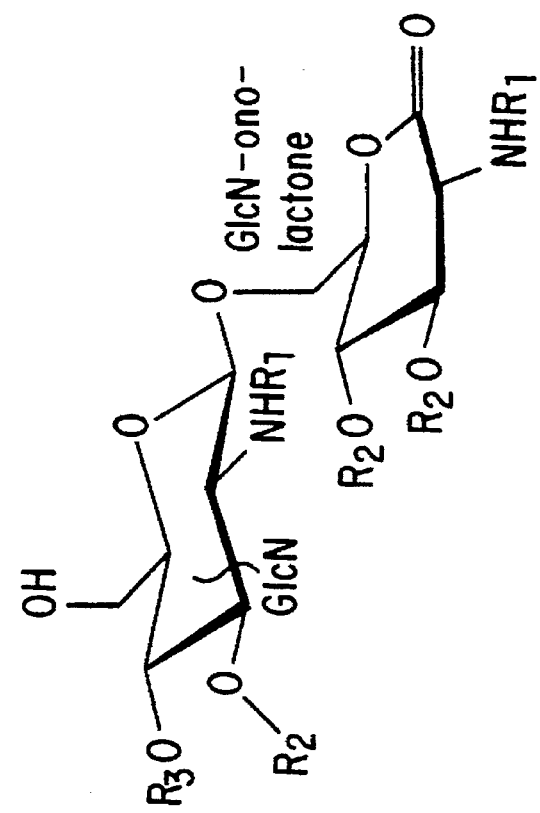
FIG. 13 shows the lipid A structures that are claimed in this patent application. These structures are based on the structures shown in FIG. 10. However, in addition to the structures of *R. leguminosarum* bv. phaseoli CE3 lipid A, other structural variations are also claimed that have different fatty acyl and acyloxyacyl groups than those structures given in FIG. 10. In addition, structures with and without GalA at the 4' position, and with and without phosphate at the 4' position are also shown. These structural variations are potential therapeutic agents based on importance of the type of fatty acyl substituents, and the presence of phosphate for biological activity (described herein).
Figure 13A:
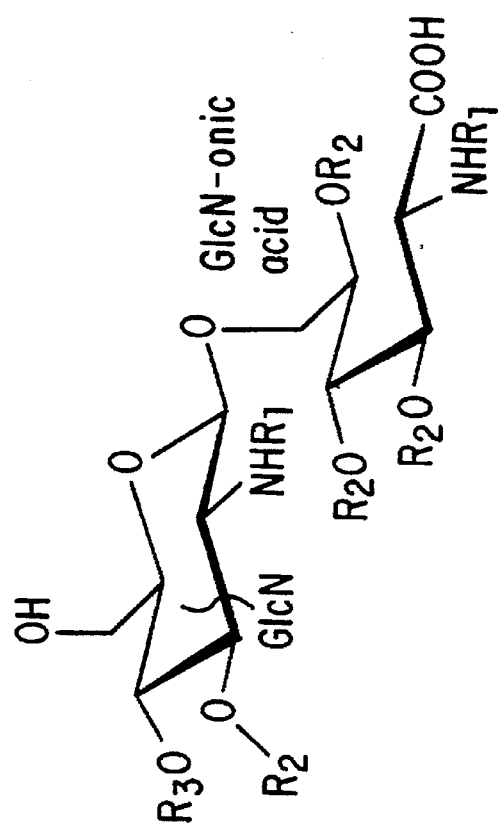
Figure 13C:
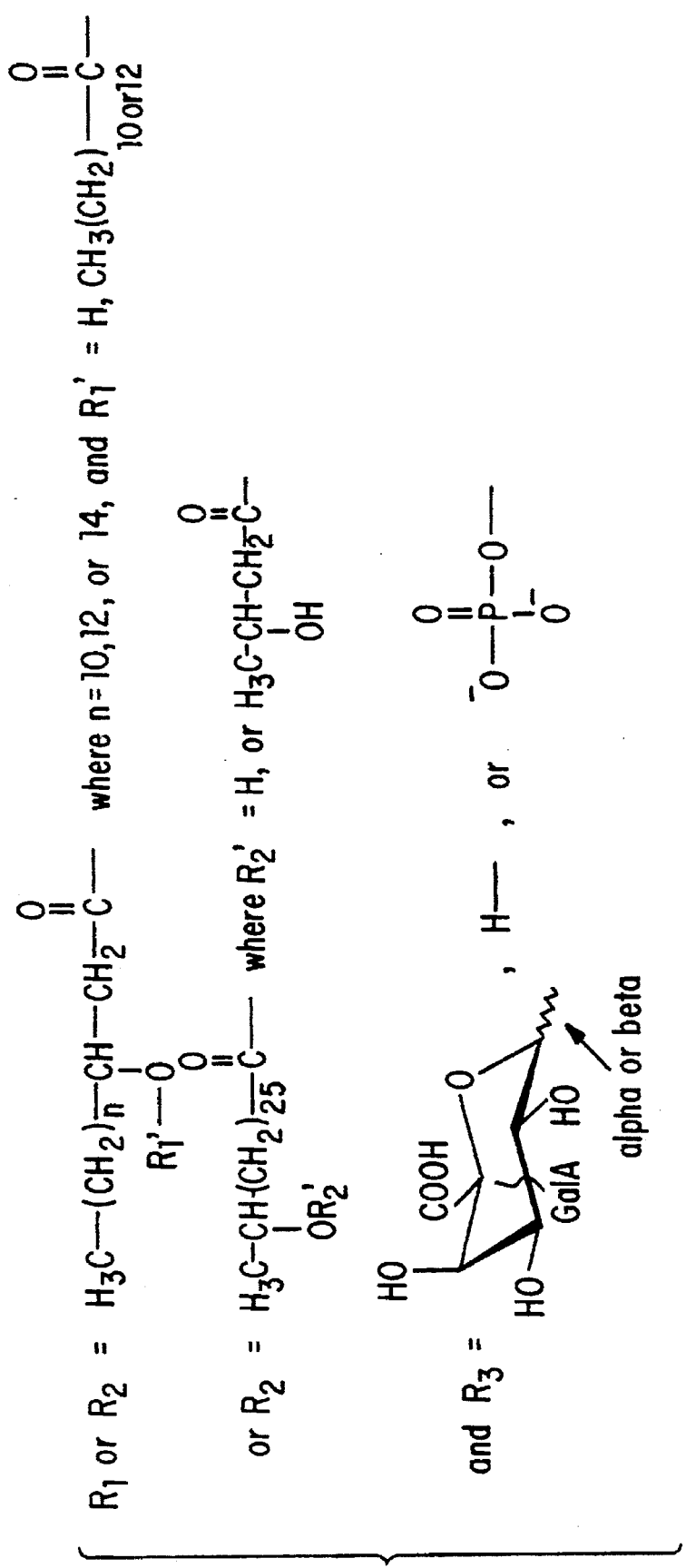

FIG. 10 shows the stimulation of MNC to release IL-1 by *R. leguminosarum* lipid A. The top panel shows that the lipid A, but not the intact LPS, can stimulate the release of IL-1 in the same concentration range as that for the positive control (the LPS from *S. friedenau*), but is less active at low concentrations than the LPS from *S. friedenau*. FIG. 11 shows the stimulation of IL-6 production by *R. leguminosarum* lipid A and LPS. The results are similar to those shown for IL-1 (FIG. 10), except that the level of IL-6 stimulation appears to be much less than that for IL-1. FIG. 12 shows the results of a second experiment examining the stimulation of IL-6. In this experiment the Rhizobium lipid A, in the high concentration range, appears to be as effective as the positive control (the *S. friedenau* LPS). However, unlike the positive control, the stimulation by the Rhizobium lipid A is much more concentration dependent than that from *S. friedenau*, dropping rapidly in activity at dilutions less than 1 mg/mL while *S. friedenau* LPS remained active at concentrations as low as 0.1 ng/mL.

The above experiments show that the Rhizobium lipid A, but not LPS, can stimulate the release of both IL-1 and IL-6 from MNC. The lipid A is more active at stimulating the release of IL-1 than IL-6, and the active concentration of the Rhizobium lipid A is at the higher end of the concentration range when compared with that of the LPS from *S. friedenau*.

FIG. 9 shows that the Rhizobium lipid A varies greatly in structure from that for *E. coli*. These structural variations involve those components that are crucial for the immunostimulatory properties and toxicity of endotoxins; namely, the phosphate and the fatty acyl substituents. It has been well established through the analysis of modified lipid A, and synthetic molecules that the phosphate groups on both the 1 and 4' positions (26,31), the presence acyloxyacyl fatty acids (26,31), and the chain length of the fatty acids (26,31), play important roles in determining the biological activities of these molecules.

The novel, purified lipid A analogs, as well as the heterogeneous mixtures described herein, of the present invention could also be used in methods of enhancing the antigenicity of a vaccine preparation comprising adding to the vaccine preparation a suitable amount of any of the analogs of the novel lipid A or that lipid A itself.

Furthermore, a method is provided for using the LPS from lipid A in a method of stimulating the immune system in a subject comprising administering to the subject an immune system stimulating amount of a purified LPS from *R. leguminosarum*. In particular, the lipid A of this bacterium has been shown to produce increased amounts of IL-1. In addition, the lipid A of this invention can be used to stimulate the production of increased amounts of IL-1 and IL-6.

Mechanism of Antagonism

Present evidence indicates that endotoxins act via direct interaction with the CD14 cell surface receptor and/or first bind to a serum protein, an LPS binding protein (LBP), and then the LPS-LPB complex is recognized by the CD14 receptor. These interactions trigger a signal transduction cascade that ultimately results in the production of cytokines. The biochemical basis for the transduction steps has not been completely defined. It is thought that an LPS antagonist would act by inhibiting the binding of the LPS to the surface receptor, to LBP, or of an LPS-LBP complex to CD14. However, the phosphate moeity on lipid A is required for maximum toxicity and also results in an optimal three dimensional conformation for binding to the surface receptor or to LBP and/or the lipid A-LBP complex to CD14.

Treatment of Other LPS Mediated Disorders

Other LPS mediated disorders could be treated with the purified analogs of this invention. For instance, Lyme disease (*Borrelia burgdorferi*) is believed to harbor an LPS (or endotoxin) which is responsible for the autoimmune-like response of the afflicted subject. Other LPS mediated disorders would be readily recognized as treatable by one skilled in the art.

Treatment Methods

Methods of treating septic shock in a subject using the compositions of the present invention are provided. For example, in one such method an amount of purified lipid A of Rhizobium leguminosarum is administered to the subject which is specifically capable of competing with the lipid binding protein of a gram(—) bacteria associated with septic shock. One way this inhibition can occur is the subject purified lipid A binds the relevant immune system related proteins or receptors and thereby prevents the formation of a bond between LPS binding protein and the toxic lipid A. Another possible mechanism of inhibition results from the binding of the subject lipid A to a receptor, e.g. the CD14 receptor on the macrophage, such that a less toxic (and potentially non-toxic) lipid A occupies available receptor sites and thereby causes a less severe systemic response.

The purified lipid A analogs of the present invention may be administered orally, parenterally (e.g., intravenously), by intramuscular injection, by intraperitoneal injection, topically, transdermally, or the like, although parenteral intravenous administration is typically preferred, especially in acute cases of endotoxicosis. The exact amount of such lipid A analogs required will vary from subject to subject, depending on the species, age, weight and general condition of the subject, the severity of the disease that is being treated, the particular compound used, its mode of administration, and the like. Thus, it is not possible to specify an exact amount. However, an appropriate amount may be determined by one of ordinary skill in the art using only routine experimentation given the teachings herein and optimization procedures known in the art. Generally, dosage will approximate that which is typical for suitable LPS or lipid A activation of target cells (generally in the ng/kg range), preferably in the range of about 0.0001 mg/patient to 600 mg/patient. More preferable ranges are about 0.001 mg/patient to 350 mg/patient. Most preferable ranges are from 0.01 to 100 mg/patient. One skilled in the art, however, could readily elucidate other dosage ranges and regimens and the above are expressly intended to be non-limiting. See, e.g., *Remington's Pharmaceutical Sciences* (latest edition).

Depending on the intended mode of administration, the lipid A analogs of the present invention can be in pharmaceutical compositions in the form of solid, semi-solid or liquid dosage forms, such as, for example, tablets, suppositories, pills, capsules, powders, liquids, suspensions, lotions, creams, gels, or the like, preferably in unit dosage form suitable for single administration of a precise dosage. The compositions will include, as noted above, an effective amount of the selected compound in combination with a pharmaceutically acceptable carrier and, in addition, may include other medicinal agents, pharmaceutical agents, carriers, adjuvants, diluents, etc. By "pharmaceutically acceptable" is meant a material that is not biologically or otherwise undesirable, i.e., the material may be administered to an individual along with the selected compound without causing any undesirable biological effects or interacting in a deleterious manner with any of the other components of the pharmaceutical composition in which it is contained.

For solid compositions, conventional nontoxic solid carriers include, for example, pharmaceutical grades of mannitol, lactose, starch, magnesium stearate, sodium saccharin, talc, cellulose, glucose, sucrose, magnesium carbonate, and the like. Liquid pharmaceutically administrable compositions can, for example, be prepared by dissolving, dispersing, etc. an active compound as described herein and optional pharmaceutical adjuvants in an excipient, such as, for example, water, saline, aqueous dextrose, glycerol, ethanol, and the like, to thereby form a solution or suspension. If desired, the pharmaceutical composition to be administered may also contain minor amounts of nontoxic auxiliary substances such as wetting or emulsifying agents, pH buffering agents and the like, for example, sodium acetate, sorbitan monolaurate, triethanolamine sodium acetate, triethanolamine oleate, etc. Actual methods of preparing such dosage forms are known, or will be apparent, to those skilled in this art; for example, see *Remington's Pharmaceutical Sciences* (latest edition).

For oral administration, fine powders or granules may contain diluting, dispersing, and/or surface active agents, and may be presented in water or in a syrup, in capsules or sachets in the dry state, or in a nonaqueous solution or suspension wherein suspending agents may be included, in tablets wherein binders and lubricants may be included, or in a suspension in water or a syrup. Where desirable or necessary, flavoring, preserving, suspending, thickening, or emulsifying agents may be included. Tablets and granules are preferred oral administration forms, and these may be coated.

Parenteral administration, if used, is generally characterized by injection. Injectables can be prepared in conventional forms, either as liquid solutions or suspensions, solid forms suitable for solution or suspension in liquid prior to injection, or as emulsions. A more recently revised approach for parenteral administration involves use of a slow release or sustained release system, such that a constant level of dosage is maintained. See, e.g., U.S. Pat. No. 3,710,795, which is incorporated by reference herein.

Vaccines

The lipid A analogs of this invention can be used in the construction of a vaccine comprising an immunogenic mount of the A analog(s) and a pharmaceutically acceptable carrier. The vaccine can be the entire lipid A (or heterogenous mixtures thereof) or an immunogenic portion thereof. The vaccine can also be potentially cross-reactive with antibodies to other lipid A analogs. The vaccine can then be used in a method of preventing septic shock or other complications of gram(—) bacteria infection (including LPS-mediated disorders such as Lyme disease and LPS-mediated exacerbation of latent/active viral infectious such as HIV-1, cytomegaloviruses, herpes simplex viruses and influenza viruses).

Immunogenic mounts of lipid A analogs can be determined using standard procedures. Briefly, various concentrations of a putative specific immunoreactive lipid A analogs are prepared, administered to an animal and the immunological response (e.g., the production of antibodies) of an animal to each concentration is determined.

The pharmaceutically acceptable carrier in the vaccine of the instant invention can comprise saline or other suitable carriers (Arnon, R. (Ed.) *Synthetic Vaccines* I:83–92, CRC Press, Inc., Boca Raton, Fla. 1987). An adjuvant can also be a part of the carrier of the vaccine, in which case it can be selected by standard criteria based on the lipid A used, the mode of administration and the subject (Arnon, R. (Ed.), 1987). Methods of administration can be by oral or sublingual means, or by injection, depending on the particular vaccine used and the subject to whom it is administered.

It can be appreciated from the above that the vaccine can be used as a prophylactic or a therapeutic modality. Thus, the invention provides methods of preventing or treating gram (—) bacteria associated septic shock and associated diseases by administering the vaccine to a subject.

Adjuvants

The novel, purified lipid A structures of the present invention may be used as adjuvants in a vaccine preparation. As an adjuvant, the lipid A will enhance the immune response to the immunogen of the vaccine preparation without concomitant adverse reactions. As such, a vaccine preparation containing the lipid A as an adjuvant along with whole killed or partial gram(—) bacteria could be used to vaccinate against a subsequent challenge from other gram (—) bacteria. Likewise, the immune response to viral immunogens could be enhanced utilizing the immunostimulatory effect of the lipid A described herein.

Immunostimulation

In addition, the novel, purified lipid A structures disclosed herein may be used to directly stimulate the immune system. In such procedures, the lipid A would be administered as described above to a patient or subject that is immune-compromised. It is important to note that the mechanism of action is not necessarily the same as that described for adjuvants and vaccines above. Instead, the purified lipid A is used to directly stimulate cytokine production, where these increased cytokines then ameliorate the condition of the immune-compromised patient.

Antibodies

Antibodies can be made as described in Harlow and Lane, *Antibodies; A Laboratory Manual*, Cold Spring Harbor Laboratory, Cold Spring Harbor, N.Y., 1988. Briefly purified lipid A from *R. leguminosarum* can be injected into an animal or other subject in an amount and in intervals sufficient to elicit an immune response. Antibodies can either be purified directly, or spleen cells can be obtained from the animal. The cells are then fused with an immortal cell line and screened for antibody secretion. The antibodies can be used to screen samples for cells containing the antigen. The presence of Rhizobium leguminosarum can then be detected in a sample using the antibodies.

Although the present invention has been described with reference to specific details of certain embodiments thereof, it is not intended that such details should be regarded as limitations upon the scope of the invention except as and to the extent that they are included in the accompanying claims. In addition, all references cited herein in the text of this specification or by citation to reference numbers corresponding to those enumerated below are herein incorporated in their entirety.

References

1. Alving C. 1992. Lipid A and liposomes containing lipid A as adjuvants for vaccines. In: Morrison D. C. and J. L. Ryan, (eds.), Bacterial endotoxic lipopolysaccharides, Volume II, Immunopharmacology and pathophysiology, CRC Press, Boca Raton, Ann Arbor, London, Tokyo.
2. Arend W. P. 1991. Interleukin 1 receptor antagonist: a new member of the interleukin 1 family. J. Clin. Invest. 88:1445–1451.
3. Beutler B. and A. Cerami. 1988. Tumor necrosis, cachexia, shock, and inflammation: a common mediator. Ann. Rev. Biochem. 57:505–518.
4. Bhat U. R. and R. W. Carlson. 1992. A new method for the analysis of amide-linked hydroxy fatty acids in lipid-As from gram-negative bacteria. Glycobiology 2:535–539.
5. Bhat U. R., H. Mayer, A. Yokota, R. I. Hollingsworth, and R. W. Carlson. 1991. Occurrence of lipid A variants with 27-hydroxyoctaeosanoic acid in lipopolysaccharides from the Rhizobiaceae group. J. Bacteriol. 173:2155–2159.
6. Bogard W. C., Jr., S. A. Siegel, A. O. Leone, E. Damiano, D. J. Shealy, T. M. Ely, B. Frederick, M. A. Mascelli, R. C. Siegel, B. Machielse, D. Naveh, P. M. Kaplan, and P. E. Daddona. 1993. Human monoclonal antibody HA-1A binds to endotoxin via an epitope in the lipid A domain of lipopolysaccharide. J. Immunol. 150:4438–4449.
7. Bogard W. C. Jr. and S. A. Siegel. 1991. The human monoclonal antibody HA-1A: Studies on the epitope location with the endotoxin molecule and epitopic exposure on the surface of viable Gram-negative bacteria. Circ. Shock 34:119.
8. Carlson R. W., S. Kalembasa, D. Turowski, P. Pachori, and K. D. Noel. 1987. Characterization of the lipopolysaccharide from a *Rhizobium phaseoli* mutant that is defective in infection thread development. J. Bacteriol. 169:,4923–4928.
9. Carlson R. W., R. E. Sanders, C. Napoli, and P. Albersheim. 1978. Host-symbiont interactions III. Purification and characterization of Rhizobium lipopolysaccharides. Plant Physiol. 62:912–917.
10. Christ W. J., T. Kawata, L. D. Hawkins, S. Kobayashi, O. Asano, and D. P. Rossignol. 1993. European patent EP-536969-A2. Dement Publications, Ltd.,
11. Davis J. 1993. New approaches to septic shock. SCRIP 1793:22–23.
12. Dinarello C. A. 1991. Interleukin-1 and interleukin-1 antagonism. Blood 77:1627–1652.
13. Fink M. P. 1993. Adoptive Immunotherapy of Gram-negative sepsis: Use of monoclonal antibodies to lipopolysaccharide. Crit. Care Med. 21 Suppl.:S32-S39.
14. Galanos C., V. Lehmann, O. Luderitz, E. Th. Rietschel, O. Westphal, H. Brade, L. Brade, M. A. Freudenberg, T. Hansen-Hagge, T. Luderitz, G. McKenzie, U. Schade, W. Strittmatter, K. Tanamoto, U. Zahringer, M. Imoto, H. Yoshimura, M. Yamamoto, T. Shimamoto, S. Kusumoto, and T. Shiba. 1984. Endotoxic properties of chemically synthesized lipid A part structures: comparison of synthetic lipid A precursor and synthetic analogues with biosynthetic lipid A precursor and free lipid A. Eur. J. Biochem. 140:221.

15. Goldman R. C., J. O. Capobianco, C. C. Doran, and A. G. Matthysse. 1992. Inhibition of lipopolysaccharide synthesis in *Agrobacterium tumefaciens* and *Aeromonas salmonicida*. J. Gen. Microbiol. 138: 1527–1533.
16. Goldman R. C., C. C. Doran, and J. O. Capobianco. 1988. Analysis of lipopolysaccharide synthesis in *Salmonella typhimurium* and *Escherichia coli* using agents which block incorporation of KDO. J. Bacteriol. 170:2185–2192.
17. Golenbock D. T., R. Y. Hampton, N. Qureshi, K. Takayama, and C. R. H. Raetz. 1991. Lipid A-like molecules that antagonize the effects of endotoxins on human monocytes. J. Biol. Chem. 266: 19490–19498.
18. Greenman R. L., R. M. H. Schein, M. A. Martin, and et al. 1991. A controlled clinical trial of E5 monoclonal IgM antibody to endotoxin in the treatment of Gram-negative sepsis. JAMA 266:1097–1102.
19. Krauss J. H., U. Seydel, J. Weckesser, and H. Mayer. 1989. Structural analysis of the nontoxic lipid A of *Rhodobacter capsulatus* 37b4. Eur. J. Biochem. 180:519–526.
20. Lee J.-D., K. Kato, P. S. Tobias, T. N. Kirkland, and R. J. Ulevitch. 1992. Transfection of CD14 into 70Z/3 cells dramatically enhances the sensitivity to complexes of lipopolysaccharide (LPS) and LPS binding protein. J. Exp. Med. 175:1697–1705.
21. Loppnow H., H. Brade, I. Durrbaum, C. A. Dinarello, S. Kusomoto, E. Th. Rietschel, and H.-D. Flad. 1989. Interleukin 1 induction-capacity of defined lipopolysaccharides partial structures. J. Immunol. 142:3229.
22. Loppnow H., P. Libby, M. Freudenberg, J. H. Krauss, J. Weckesser, and H. Mayer. 1990. Cytokine induction by lipopolysaccharide (LPS) corresponds to lethal toxicity and is inhibited by nontoxic *Rhodobacter capsulatus* LPS. Infect. Immun. 58:3743–3750.
23. Morrison D. C. and J. L. Ryan. 1987. Endotoxins and disease mechanisms. Ann. Rev. Med. 38:417–432.
24. Nod K. D., K. A. VandenBosch, and B. Kulpaea. 1986. Mutations in *Rhizobium phaseoli* that lead to arrested development of infection threads. J. Bacteriol. 168: 1392–1401.
25. Raetz C. R. H., R. J. Ulevitch, S. D. Wright, C. H. Sibley, A. Ding, and C. F. Nathan. 1991. Gram-negative endotoxin: an extraordinary lipid with profound effects on eukaryotic signal transduction. FASEB Journal 5:2652–2660.
26. Rietschel E. Th., L. Brade, B. Lindner, and U. Zahringer. 1992. Biochemistry of lipopolysaccharides. In: p. 3–41. Morrison D. C. and J. L. Ryan, (eds.), Bacterial endotoxic lipopolysaccharides, Volume I, Molecular biochemistry and cellular biology, CRC Press, Boca Raton, Ann Arbor, London, Tokyo.
27. Rietschel E. Th., L. Brade, U. Schade, C. Galanos, M. A. Freudenberg, O. Luderitz, S. Kusumoto, and T. Shiba. 1987. Endotoxic properties of synthetic pentaacyl lipid A precursor Ib and a structural isomer. Eur. J. Biochem. 169:27.
28. Rubin R. M., J. Noland, and J. T. Rosenbaum. 1992. Reduction of endotoxin-induced vascular permeability by monoclonal antibodies against lipopolysaccharide determinants. Circ. Shock 36:217–223.
29. Ryan J. M. and H. E. Conrad. 1974. Structural hertergeneity in the lipopolysaccharide from *Salmonella newington*. Arch. Biochem. Biophys. 162:530–535.
30. Schumann R. R., S. R. Leong, G. W. Flaggs, P. W. Gray, S. D. Wright, J. C. Mathison, P. S. Tobias, and R. J. Ulevitch. 1990. Structure and function of lipopolysaccharide binding protein. Science 249: 1429–1431.
31. Takada H. and S. Kotani. 1992. Structure-function relationships of lipid A. In: p. 107–134. Morrison D. C. and J. L. Ryan, (eds.), Bacterial endotoxic lipopolysaccharides, Volume I, Molecular biochemistry and cellular biology, CRC Press, Boca Raton, Ann Arbor, London, Tokyo.
32. Takayama K., N. Qureshi, B. Beufler, and T. N. Kirkland. 1989. Dephosphoryl lipid A from *Rhodopseudomonas sphaeroides* ATCC 17023 blocks induction of cachectin in macrophages by lipopolysaccharide. Infect. Immun. 57:1336–1338.
33. Takayama K., N. Qureshi, E. Ribi, J. L. Cantrell, and K. Amano. 1983. Use of endotoxin in cancer immunotherapy and characterization of its nontoxic but active lipid A components. In: p. 219–233. Anderson L. and F. M. Unger, (eds.), Bacterial lipopolysaccharides, American Chemical Society, Washington, D.C..
34. Tobias P. S., K. Soldau, L. Kline, J.-D. Lee, K. Kato, T. P. Martin, and R. J. Ulevitch. 1993. Cross-linking of lipopolysaccharide (LPS) to CD14 on THP-1 cells mediated by LPS-binding protein. J. Immunol. 150:3011–3021.
35. Tobias P. S., K. Soldau, and R. J. Ulevitch. 1989. Identification of a lipid A binding site in the acute phase reactant lipopolysaccharide binding protein. J. Biol. Chem. 264: 10867–10871.
36. Von Esehen K. 1992. Monphosphoryl lipid A and immunotherapy. In: Morrison D. C. and J. L. Ryan, (eds.), Bacterial endotoxic lipopolysaccharides, Volume II, Immunopharmacology and pathophysiology, CRC Press, Boca Raton, Ann Arbor, London, Tokyo.
37. Wang M.-H., W. Feist, H. Herzbeck, H. Brade, S. Kusumoto, E. Th. Rietschel, H.-D. Flad, and A. J. Ulmer. 1990. Suppressive effect of lipid A partial structures on lipopolysaccharide or lipid A-induced release of interleukin 1 by human monocytes. FEMS Microbiol. Immunol. 64:179.
38. Warren H. S., R. L. Danner, and R. S. Munford. 1992. Anti-endotoxin monoclonal antibodies. N. Engl. J. Med. 326:1153–1157.
39. Westphal O. and K. Jann. 1965. Bacterial lipopolysaccharides. Meth. Carbohydr. Chem. 5:83–91.
40. Wollenweber H.-W. and E. Th. Rietschel. 1990. Analysis of lipopolysaccharide (lipid A) fatty acids. J. Microbiol. Methods 11:195–211.
41. Wortel C. H., E. J. Ziegler, and S. J. H. Van Deventer. 1991. Therapy of Gram-negative sepsis in man with anti-endotoxin antibodies: A review. Prog. Clin. Biol. Res. 367: 161–178.
42. Wright S. D., R. A. Ramos, P. S. Tobias, R. J. Ulevitch, and J. C. Mathison. 1990. CD14, a receptor for complexes of lipopolysaccharide (LPS) and LPS binding protein. Science 249: 1431–1433.
43. York W. S., A. G. Darvill, M. McNeil, T. T. Stevenson, and P. Albersheim. 1985. Isolation and characterization of plant cell walls and cell wall components. Meth. Enzymol. 118:3–40.
44. Ziegler E. J., C. J. Jr. Fisher, C. L. Sprung, and et al. 1991. Treatment of Gram-negative bacteremia and septic shock with HA-1A human monoclonal antibody against endotoxin-A randomized, double-blind, placebo-controlled trial. N. Engl. J. Med. 324:429–436.
45. Ziegler E. J., J. A. McCutchan, J. Fierer, and et al.. 1982. Treatment of Gram-negative bacteremia and shock with human antiserum to a mutant *Escherichia coli*. N. Engl. J. Med. 307:1225–1230.
46. Ohno, K., Nishiyama, H., and Nagase, H. 1979. Tetrahedr Lett. 45:4405–4406.

47. Bhat, U. R., Bhagyalakshmi, S. K., and Carlson, R. W. 1991. Carbohydr. Res. 220:219–227.
48. Demary, M., Puzo, G., and Asselineau, J. 1977. Nouv. J. Chimie 2:373–378.
49. Hollingsworth, R. I., Carlson, R. W., Garcia, F., and Gage, D. A. 1990. J. Biol. Chem. 265:12752.
50. Hollingsworth, R. I., Carlson, R. W., Garcia, F., and Gage, D. A. 1989. J. Biol. Chem. 264:9294–9299.
51. Zhang, Y., Hollingsworth, R. I., and Priefer, U. B. 1992. Carbohydr. Res. 231:261–271.
52. Russa, R., Luderitz, O., and Rietschel, E. T. 1985. Arch. Microbiol. 141:284–289.
53. Hollingsworth, R. I. and Lill-Elghanian, D. A. 1989. J. Biol. Chem. 264:14039–14042.
54. Segovia, L., Young, J. P. W., and Martinez-Romero, E. 1993. Int. J. Syst. Bacteriol. 43:374–377.
55. Kotani, S. and Takada H. 1990. Adv. Exp. Med. Biol. 256:13–44.

What is claimed is:

1. A method of treating toxic shock in a subject in need of such treatment, comprising administering to the subject an effective mount of a compound of formula I:

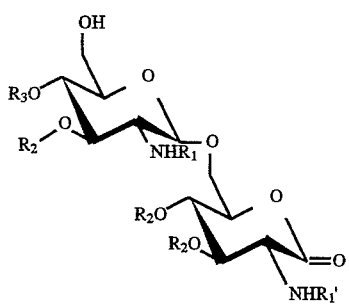

(I)

or formula II:

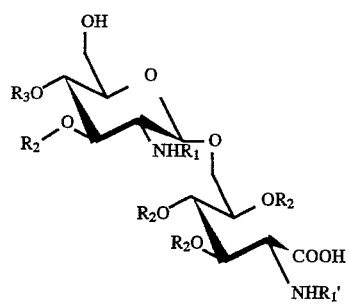

(II)

wherein, for formulas I and II, $R_1$ and $R_1'$ are independently $H_3C$—$(CH_2)_m$—$COR_4H$—$CH_2$—$CO$— where $R_4$ is H, $H_3C$—$(CH_2)_{10}$—$CO$— or $H_3C$—$(CH_2)_{12}$—$CO$—, and m is 10, 12 or 14;

$R_2$ is $H_3C$—$CHOR_5$—$(CH_2)_{25}$—$CO$— or $H_3C$—$(CH_2)_nCOR_6H$—$CH_2$—$CO$— where $R_5$ is H or $H_3C$—$CHOH$—$CH_2$—$CO$—, $R_6$ is H, $H_3C$—$(CH_2)_{10}$—$CO$— or $H_3C$—$(CH_2)_{12}$—$CO$—, and n is 10, 12 or 14; and $R_3$ is H, —$PO_4$ or

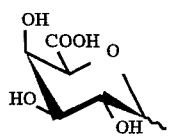

where the wavy line represents an alpha or beta alkyl linkage.

2. The method of claim 1, wherein, for formulas I and II, $R_1$ is $H_3C$—$(CH_2)_{10}$—$CHOH$—$CH_2$—$CO$—;
$R_1'$ is $H_3C$—$(CH_2)_{12}$—$CHOH$—$CH_2$—$CO$—;
$R_2$ is $H_3C$—$CHOR_4$—$(CH_2)_{25}$—$CO$— or $H_3C$—$(CH_2)_{10}CHOH$—$CH_2$—$CO$— where $R_4$ is $H_3C$—$CH(OH)$—$CH_2$—$CO$—; and
$R_3$ is

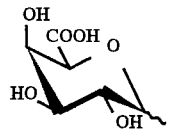

where the wavy line represents an alpha alkyl linkage.

3. A method of preventing toxic shock in a subject in need of such prevention, comprising administering to the subject an effective amount of a compound of formula I:

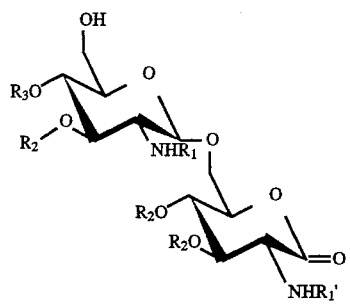

(I)

or formula II:

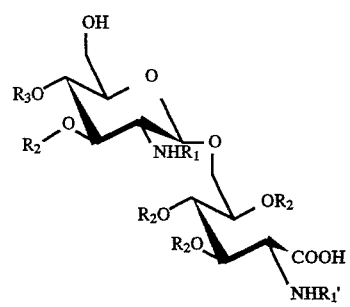

(II)

wherein, for formulas I and II, $R_1$ and $R_1'$ are independently $H_3C$—$(CH_2)_m$—$COR_4H$—$CH_2$—$CO$— where $R_4$ is H, $H_3C$—$(CH_2)_{10}$—$CO$— or $H_3C$—$(CH_2)_{12}$—$CO$—, and m is 10, 12 or 14;

$R_2$ is $H_3C$—$CHOR_5$—$(CH_2)_{25}$—$CO$— or $H_3C$—$(CH_2)_nCOR_6H$—$CH_2$—$CO$— where $R_5$ is H or $H_3C$—$CHOH$—$CH_2$—$CO$—, $R_6$ is H, $H_3C$—$(CH_2)_{10}$—$CO$— or $H_3C$—$(CH_2)_{12}$—$CO$—, and n is 10, 12 or 14; and $R_3$ is H, —$PO_4$ or

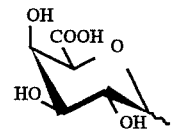

where the wavy line represents an alpha or beta alkyl linkage.

4. The method of claim 3, wherein, for formulas I and II, $R_1$ is $H_3C$—$(CH_2)_{10}$—$CHOH$—$CH_2$—$CO$—;
$R_1'$ is $H_3C$—$(CH_2)_{12}$—$CHOH$—$CH_2$—$CO$—;
$R_2$ is $H_3C$—$CHOR_4$—$(CH_2)_{25}$—$CO$— or $H_3C$—$(CH_2)_{10}CHOH$—$CH_2$—$CO$— where $R_4$ is $H_3C$—$CH(OH)$—$CH_2$—$CO$—; and $R_3$ is

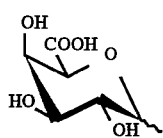

where the wavy line represents an alpha alkyl linkage.

5. A method of treating or preventing a lipopolysaccharide mediated disorder in a subject in need of such treatment or prevention, comprising administering to the subject a lipopolysaccharide mediated disorder inhibiting amount of a compound of formula I:

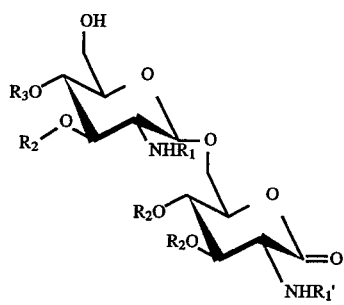

or formula II:

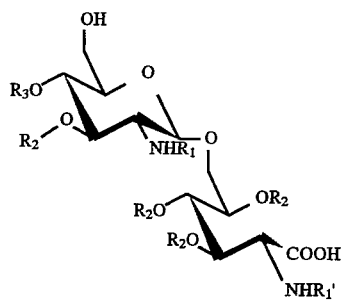

wherein, for formulas I and II, $R_1$ and $R_1'$ are independently $H_3C-(CH_2)_m-COR_4H-CH_2-CO-$ where $R_4$ is H, $H_3C-(CH_2)_{10}-CO-$ or $H_3C-(CH_2)_{12}-CO-$, and m is 10, 12 or 14;

$R_2$ is $H_3C-CHOR_5-(CH_2)_{25}-CO-$ or $H_3C-(CH_2)_n COR_6H-CH_2-CO-$ where $R_5$ is H or $H_3C-CHOH-CH_2-CO-$, $R_6$ is H, $H_3C-(CH_2)_{10}-CO-$ or $H_3C-(CH_2)_{12}-CO-$, and n is 10, 12 or 14; and $R_3$ is H, $-PO_4$ or

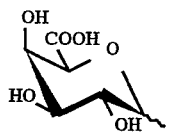

where the wavy line represents an alpha or beta alkyl linkage.

6. The method of claim 5, wherein, for formulas I and II, $R_1$ is $H_3C-(CH_2)_{10}-CHOH-CH_2-CO-$;

$R_1'$ is $H_3C-(CH_2)_{12}-CHOH-CH_2-CO-$;

$R_2$ is $H_3C-CHOR_4-(CH_2)_{25}-CO-$ or $H_3C-(CH_2)_{10}CHOH-CH_2-CO-$ where $R_4$ is $H_3C-CH(OH)-CH_2-CO-$; and $R_3$ is

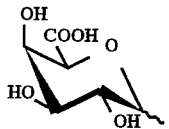

where the wavy line represents an alpha alkyl linkage.

7. The method of claim 5, wherein the lipopolysaccharide mediated disorder is septic shock.

* * * * *